(12) United States Patent
Lonergan

(10) Patent No.: US 11,102,922 B2
(45) Date of Patent: Aug. 31, 2021

(54) GROWTH OF CRYO-SPROUTS

(71) Applicant: The Vista Institute LLC, Eden Prairie, MN (US)

(72) Inventor: Dennis Lonergan, Long Lake, MN (US)

(73) Assignee: THE VISTA INSTITUTE LLC, Eden Prairie, MN (US)

( * ) Notice: Subject to any disclaimer, the term of this patent is extended or adjusted under 35 U.S.C. 154(b) by 65 days.

(21) Appl. No.: 15/990,137

(22) Filed: May 25, 2018

(65) Prior Publication Data

US 2018/0271036 A1   Sep. 27, 2018

Related U.S. Application Data

(62) Division of application No. 14/994,833, filed on Jan. 13, 2016, now Pat. No. 10,015,936.

(60) Provisional application No. 62/103,378, filed on Jan. 14, 2015.

(51) Int. Cl.
| | | |
|---|---|---|
| *A01C 1/02* | (2006.01) |
| *A01G 9/029* | (2018.01) |
| *C12N 5/04* | (2006.01) |
| *A01H 5/10* | (2018.01) |
| *A01G 22/15* | (2018.01) |
| *A01G 22/25* | (2018.01) |

(Continued)

(52) U.S. Cl.
CPC .............. *A01C 1/02* (2013.01); *A01G 9/029* (2018.02); *A01G 22/15* (2018.02); *A01G 22/25* (2018.02); *A01G 22/40* (2018.02); *A01H 5/10* (2013.01); *C12N 5/04* (2013.01); *A01G 31/02* (2013.01)

(58) Field of Classification Search
CPC ........ A01G 22/00; A01G 9/0293; A01G 9/02; A01G 31/02; A01G 9/029
See application file for complete search history.

(56) References Cited

U.S. PATENT DOCUMENTS 3,768,201 A   10/1973   Yoo
3,906,663 A    9/1975   Peng et al.
(Continued)

FOREIGN PATENT DOCUMENTS

GB   2089632 A   6/1982
RU   2025961 C1   1/1995
(Continued)

OTHER PUBLICATIONS

Extended European Search Report issued in related European Patent Application No. 16737809.0 dated Aug. 10, 2018.
(Continued)

*Primary Examiner* — Magdalena Topolski
(74) *Attorney, Agent, or Firm* — Westman, Champlin & Koehler, P.A.; Z. Peter Sawicki; Visala C. Goswitz

(57) ABSTRACT

Cryo-sprouts are germinated, grown and shipped in the same covered container with reduced numbers of pathogenic organisms. Seeds are placed on a membrane in the container with sufficient water. The container with the seeds is incubated at a pathogen antagonistic temperature during the growth phase. The pathogen antagonistic temperature is preferably between about 35° F. and about 45° F. The cryo-sprouts grown according to these methods have reduced numbers of pathogenic organisms, are greener and have an extended shelf-life.

12 Claims, 9 Drawing Sheets

(51) Int. Cl.
*A01G 22/40* (2018.01)
*A01G 31/02* (2006.01)

(56) References Cited

U.S. PATENT DOCUMENTS

| | | | | |
|---|---|---|---|---|
| 3,965,614 | A * | 6/1976 | Kienholz | A01G 31/06 47/14 |
| 4,006,557 | A * | 2/1977 | Sawyer | A01G 31/02 141/319 |
| 4,124,953 | A * | 11/1978 | Patton | A01G 9/02 206/462 |
| 4,135,331 | A * | 1/1979 | Lamlee | A01G 31/02 206/815 |
| 4,180,941 | A * | 1/1980 | Korematsu | A01G 31/02 47/14 |
| 4,291,493 | A * | 9/1981 | Monson | A01G 31/02 47/14 |
| 4,292,761 | A | 10/1981 | Krave | |
| 4,330,957 | A * | 5/1982 | Davis | A01G 31/02 47/14 |
| 5,896,701 | A * | 4/1999 | Schaerer | A01G 31/02 206/815 |
| 5,927,007 | A * | 7/1999 | Oda | A01G 31/02 47/60 |
| 6,313,377 | B1 * | 11/2001 | Schipper | A01C 1/00 47/58.1 R |
| 6,689,609 | B1 * | 2/2004 | Fan | A01C 1/02 435/422 |
| 7,921,600 | B1 * | 4/2011 | Cleveland | A01G 9/16 47/69 |
| 8,375,628 | B2 * | 2/2013 | Petersen | G01N 33/0098 47/16 |
| 8,763,305 | B1 * | 7/2014 | Petersen | G01N 33/0098 47/61 |
| 8,966,813 | B2 * | 3/2015 | Petersen | G01N 33/0098 47/14 |
| 9,161,495 | B2 * | 10/2015 | Lee | A23L 7/104 |
| 9,326,455 | B2 * | 5/2016 | McClay | A01G 9/02 |
| 9,334,086 | B2 * | 5/2016 | Bean | B65D 51/16 |
| 2002/0130078 | A1 | 9/2002 | Tonkin et al. | |
| 2003/0079403 | A1 | 5/2003 | Hsien | |
| 2005/0055879 | A1 * | 3/2005 | Darlington | F24F 3/16 47/62 R |
| 2009/0077873 | A1 * | 3/2009 | Petersen | G01N 33/0098 47/14 |
| 2013/0108721 | A1 | 5/2013 | Lee | |
| 2014/0237895 | A1 * | 8/2014 | Samadpour | A01C 1/02 47/58.1 R |

FOREIGN PATENT DOCUMENTS

| | | |
|---|---|---|
| RU | 2048058 C1 | 11/1995 |
| RU | 2002111550 A | 12/2004 |
| SU | 1537181 A1 | 1/1990 |

OTHER PUBLICATIONS

Search Report and Written Opinion issued in related International Patent Application No. PCT/US2016/013230 dated Jun. 2, 2016.
Liana: "Graines germees : Germination et preparation avec ou sans germoir." May 20, 2006 XP055742878, retrieved from the internet: URL:http://www.cfaitmaison.com/germs/germination.html [retrieved on Oct. 22, 2020].
Anonymous: "Faire germer les graines : comment faire ? (2eme partie)—Le Jardin des Medicinales", Aug. 7, 2012, XP055742881, Retrieved from the Internet: URL:https://le-jardin-des-medicinales.com/faire-germer-2eme-partie/ [retrieved on Oct. 22, 2020].
Examination Report issued for EP patent application serial No. 16737809.0, dated Nov. 2, 2020.

* cited by examiner

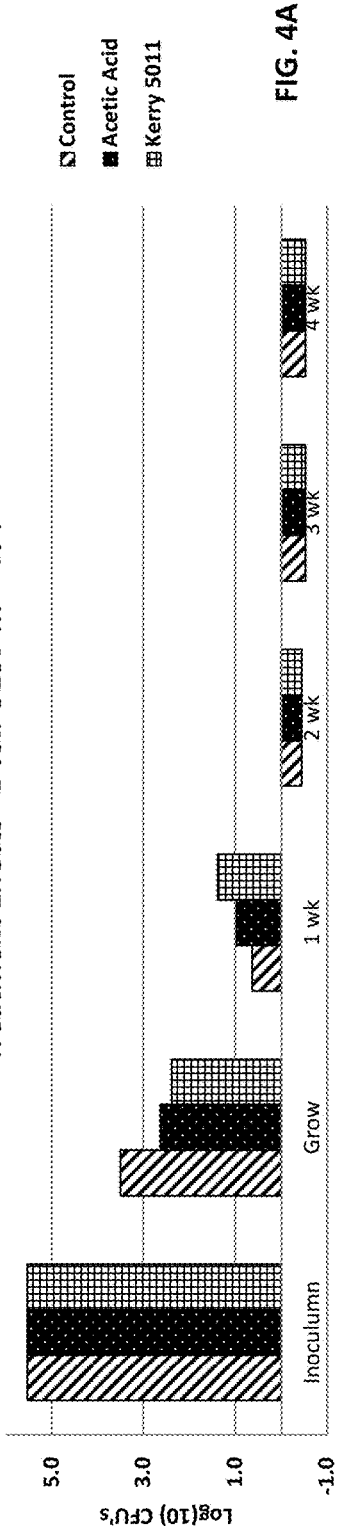
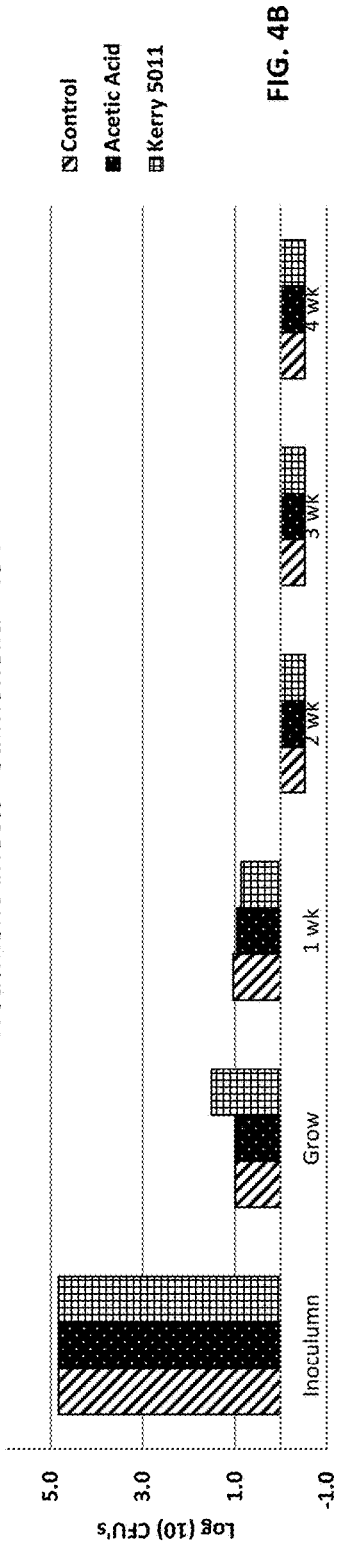
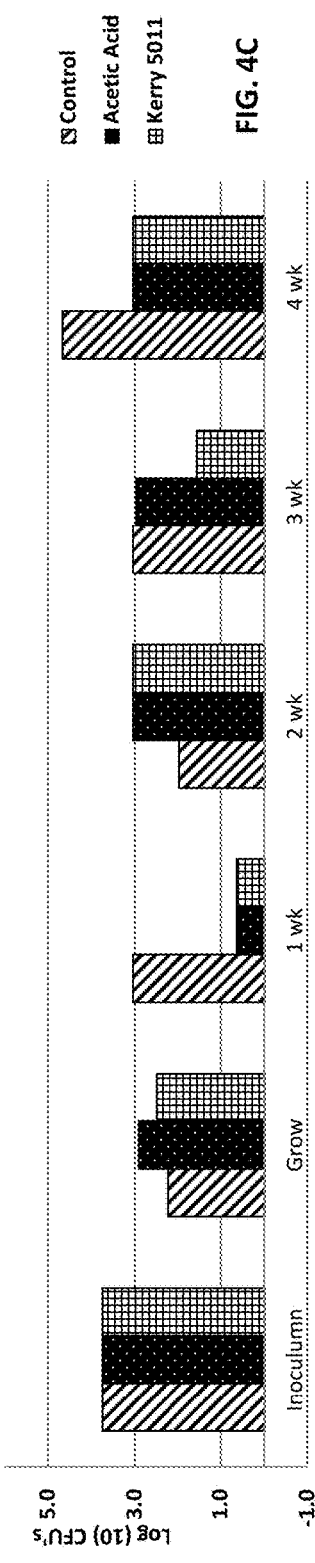
FIG. 4A
FIG. 4B
FIG. 4C

GROWTH OF CRYO-SPROUTS

CROSS-REFERENCE TO RELATED APPLICATION

The present application is a divisional of and claims the benefit of U.S. non-provisional patent application Ser. No. 14/994,833, filed Jan. 13, 2016, which is based on and claims the benefit of U.S. provisional patent application Ser. No. 62/103,378, filed Jan. 14, 2015, the contents of which are hereby incorporated by reference in their entirety.

FIELD

The present description generally relates to growing sprouts and microgreens for consumption.

BACKGROUND

Sprouts and microgreens are foods produced by exposing seeds to water, light, and other conditions that allow the seeds to germinate and grow into tiny plants. Seeds that germinate into edible small plant forms include, for example, alfalfa, clover, cress, kale, mung bean, radish, mustard, broccoli, onions, flax, green peas, sunflower, corn, wheat, oats, barley, rye, soybeans, and others.

Seeds used in the growth of sprouts are generally purchased and/or obtained from farms. There are no particular precautions to keep the seeds clean and microbe free thus the seeds may contain bacteria, viruses, fungi, or other organisms that can be harmful to public health. The presence of microbial pathogens such as *E. coli* O157:H7, *Salmonella*, *Listeria* may be harmful to the health of the consumer. In addition, seeds may be contaminated with other organisms that may interfere with the quality of sprouts by imparting to them a bad flavor or color or by reducing shelf life. The addition of water as well as the handling and manipulation of the seeds during the growth and packaging of the sprouts can also introduce undesirable microorganisms.

Sprouts and microgreens have been grown by methods that include rinsing the seeds, sanitizing the seeds, placing the seeds in trays or drums at ambient temperature to allow for growth to marketable size. When seeds are sprouted in rotating drums, the seeds are watered approximately every 30 minutes. When the sprouts are fully grown (~4-5 days), the sprouts are rinsed, dried and packaged for sale in either bags or trays. The safety of the sprouts is generally reliant on the disinfection of the seed and the testing of waste irrigation water for the presence of pathogens. The disinfection is not reliable and furthermore the pathogenic organisms may be introduced and allowed to grow during the manufacturing process. Alternatively, seeds for sprouts or microgreens may be placed in retail containers, with irrigation holes in the bottom, over a foam or an absorbent material such as cellulose and sprouted in the same container in which they may ultimately be delivered to consumers. The containers are placed on trays and the growing sprouts are irrigated from overhead or from the bottom tray with the seeds being irrigated periodically via holes in the container. At the end of the growth cycle, the prior art containers are capped with a lid, labeled and sent to the market with open irrigation holes, which compromises the sanitary condition of the product and its package. Again, the pathogenic organisms may be introduced and allowed to multiply easily during the growth of the sprouts, especially during irrigation.

Methods are also known that use water-retaining media such as agar in a container that can be shipped. The seeds or germinated seeds are placed directly on the water-retaining media so that the seeds use the water from the moisture-retaining layer for growth. The containers are first shipped at temperatures appropriate for growth generally about 70° F. and after several days stored at a storage temperature of about 45° F. after completion of growth. This system optionally uses two phases of temperature, one for growth and one for storage. Pathogenic bacteria could still be present and multiply rapidly during the growth phase of the sprouts leading to high levels of undesirable pathogenic bacteria.

SUMMARY

In a first aspect, the present description includes a method of growing cryo-sprouts including incubating a container including water, a membrane, and hydrated seeds at a pathogen antagonistic temperature for a growth period sufficient for growth of cryo-sprouts. The membrane is supported in the container by internal supports and the hydrated seeds are dispersed on the membrane prior to incubation. The pathogen antagonistic temperature may be between about 35° F. and about 45° F. The container may be covered with lid to form a covered container wherein the covered container is permeable to air. The seeds may be hydrated in a hydration composition, wherein the hydration composition is selected from water, a composition comprising a fermentate, a composition comprising a fermentate from a lactic acid fermenting bacteria, a composition comprising bacteriocin, a composition comprising benzoic acid, a composition comprising cranberry juice, carrot juice and/or combinations thereof. The seeds may be alfalfa, clover, kale, radish, cress, broccoli and combinations thereof. The membrane may include woven material, non-woven material, non-hygroscopic material or combinations thereof. The hydrated seeds may be primed prior to incubation at the pathogen antagonistic temperature or prior to the initiation of the growth period, wherein the priming comprises storing the hydrated seeds in the dark for at least about 1 day or longer. The method may include adding a total of about 4 to about 5 grams of water per gram of air-dried seeds. The growth period may be at least about 14 days. The first portion of the growth period may be without light. The cryo-sprouts may have a shelf-life of at least about 21 days. The method may be microbicidal or microbiostatic against *Escherichia coli* O157:H7, *Salmonella* spp., and *Listeria*.

In yet another aspect, the present description includes a method of reducing pathogenic bacteria in cryo-sprouts. The method includes incubating a container at a pathogen antagonistic temperature, the container comprising hydrated seeds, a membrane and water sufficient for growth of the cryo-sprouts, wherein the pathogen antagonistic temperature comprises a temperature below about 45° F. The container may be covered with lid to form a covered container wherein the covered container is permeable to air. The seeds may be hydrated in a hydration composition, wherein the hydration composition is selected from water, a composition comprising a fermentate, a composition comprising a fermentate from a lactic acid fermenting bacteria, a composition comprising bacteriocin, a composition comprising benzoic acid, a composition comprising cranberry juice, carrot juice and/or combinations thereof. The seeds may be alfalfa, clover, kale, broccoli and combinations thereof. The membrane may include woven material, non-woven material, non-hygroscopic material or combinations thereof. The hydrated seeds may be primed prior to incubation at the pathogen antagonistic temperature or prior to the initiation of the growth period, wherein the priming comprises storing the hydrated seeds in the dark for at least about 1 day or longer. The method may include adding a total of about 4 to about 5 grams of water per gram of air-dried seeds. The growth period may be at least about 14 days. The first portion of the growth period may be without light. The cryo-sprouts may have a shelf-life of at least about 21 days. The method may be microbicidal or microbiostatic against *Escherichia coli* O157:H7, *Salmonella* spp., and *Listeria*. The method may include storing the cryo-sprouts. The storage temperature may be between about 34° F. and about 42° F.

In a further aspect, the present description includes a covered container with cryo-sprouts. The product includes a container, a membrane supported above the floor of the container on internal supports, a lid to cover the container, wherein the volume between the floor of the container and the membrane is sufficient to hold an amount of water sufficient to support germination of seeds and growth of cryo-sprouts at a pathogen antagonistic temperature, wherein the covered container is permeable to air and assimilation of water occurs during the growth period of the cryo-sprouts. The pathogen antagonistic temperature may be between about 45° F. and about 35° F. The seeds may be alfalfa, clover, kale, broccoli and combinations thereof. The membrane may include woven material, non-woven material, non-hygroscopic material or combinations thereof. The container may include cryo-sprouts derived from about 15 grams to about 60 grams of air-dried seeds. The shelf-life of the cryo-sprouts may be at least about 21 days.

In another aspect, the present description includes a method of providing cryo-sprouts to a consumer. The method includes growing cryo-sprouts from hydrated seeds in a container at a pathogen antagonistic temperature wherein the container includes a membrane supported on an internal support above the floor of the container.

BRIEF DESCRIPTION OF THE DRAWINGS

FIGS. 4A-4C are bar graphs of the effect of seed hydration on growth of cryo-sprouts at 40° F. for *E. coli* O157:H7, *Salmonella* and *Listeria*, respectively.

DETAILED DESCRIPTION OF ILLUSTRATIVE EMBODIMENTS

Figure 1:
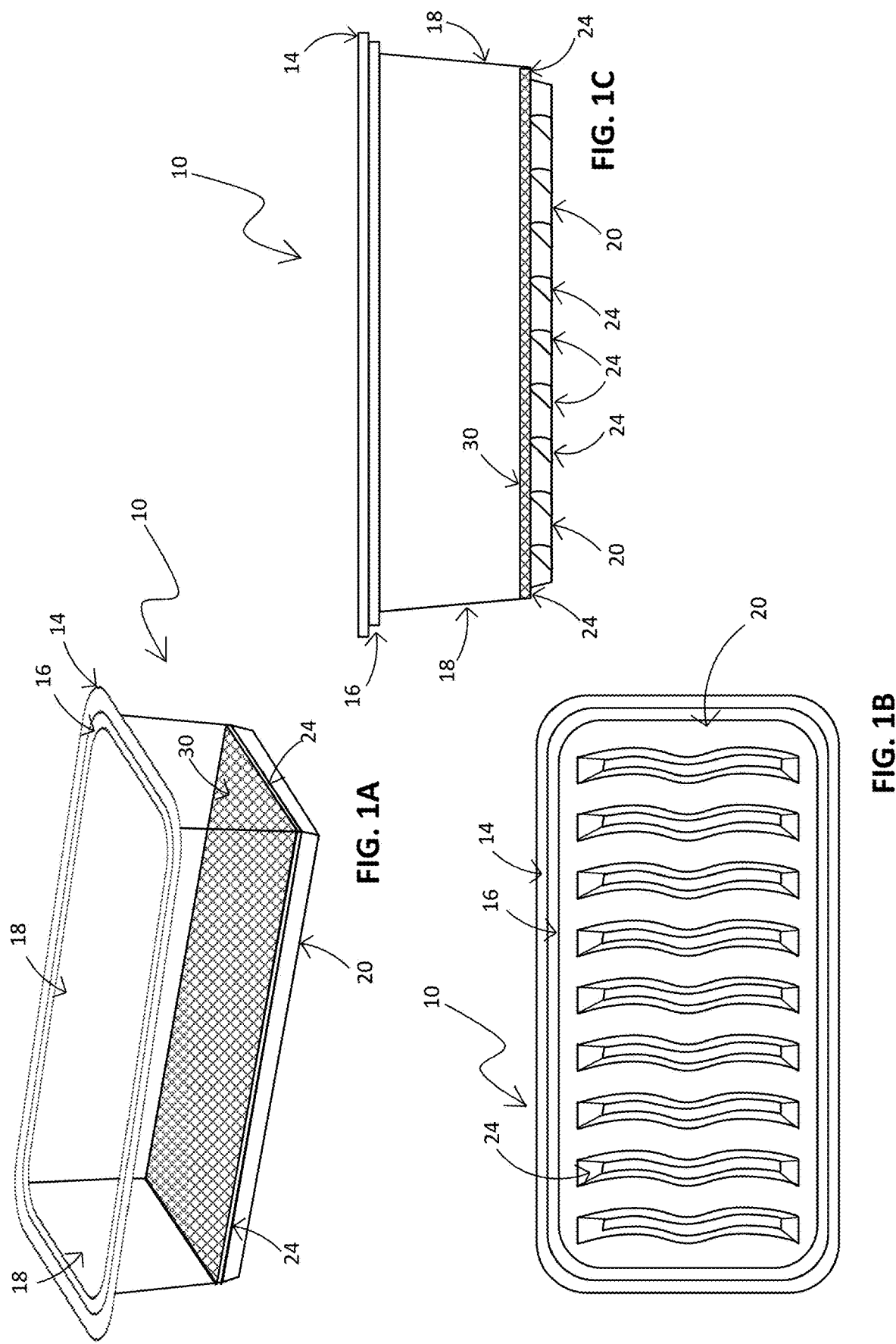
FIGS. 1A-1C are schematic diagrams of an exemplary container used for growing cryo-sprouts.

The present description relates to cryo-sprouts that can be germinated, grown, stored and/or shipped in the same container. Seeds can be placed on a membrane that is suspended above the floor of the container. In one embodiment, the container includes internal supports for supporting the membrane above the floor of the container. Water can be added to the container and the permeation rate of the water through the membrane can facilitate the dispersal of the seeds over the surface the membrane. The membrane with the dispersed seeds can rest on the internal supports near the surface of the water. The container is covered and incubated at a pathogen antagonistic temperature. In one embodiment, the pathogen antagonistic temperature can be between about 35° F. and about 45° F. During incubation, the cryo-sprouts can grow, even at the pathogen antagonistic temperature. After growth of the cryo-sprouts, the container can be stored at storage temperatures.

Surprisingly, during incubation at the pathogen antagonistic temperature, the seeds can germinate and also grow into sprouts. The sprouts grown under these conditions advantageously have decreased numbers of undesirable pathogenic bacteria. Incubation at the pathogenic antagonistic temperature can result in microbicidal activity against some pathogenic bacteria. The growth conditions can be microbiostatic against other pathogenic bacteria. Furthermore, the sprouts grown under these conditions can have a significantly extended storage period or shelf-life.

"Containers" and "trays" are used interchangeably herein and both refer to vessels that can be used to grow the sprouts.

"Cryo-sprouts" as used herein relates to sprouts grown at a pathogen antagonistic temperature. Cryo-sprouts may sometimes be referred to herein as sprouts.

Sprouts or cryo-sprouts as used herein include sprouts, microgreens, shoots or crests. Cryo-sprouts can be derived from a variety of seeds including, but not limited to, alfalfa, clover, cress, kale, mung bean, radish, mustard, broccoli, onions, flax, green peas, sunflower, corn, wheat, oats, barley, rye, soybeans, and the like.

"Pathogen antagonistic temperature" as referred to herein relates to a temperature that is not conducive to unabated growth of pathogens and/or a temperature wherein some pathogens generally do not thrive.

"Planting" as referred to herein relates to adding hydrated seeds and the appropriate amount of water to the container in which the cryo-sprouts will be grown and incubating them at a pathogen antagonistic temperature for growth of the cryo-sprouts. Planting initiates the growth phase.

"Germination" as referred to herein is the process by which a plant grows from a seed. An example of germination is the sprouting of a seedling from a seed that occurs during the growth phase or period.

"Hydration" as referred to herein is the addition of a liquid to a dormant seed.

"Priming" as referred to herein is the incubation of hydrated seeds in the dark for a period of time prior to the initiation of the growth phase.

"Growth phase" or "growth period" as referred to herein is initiated by the addition of sufficient water for growth and incubation at the pathogen antagonistic temperature. The seeds germinate and grow into cryo-sprouts during the growth phase.

"Storage phase" or "storage period" as referred to herein can begin when the growth of the cryo-sprouts is substantially complete. During the storage phase, the sprouts can be in stasis and the assimilation of water by the seeds is substantially complete. Storage phase may also be referred to as "shelf-life".

The present description includes containers having internal supports, a membrane and seeds that have been germinated and grown into sprouts in the container by the addition of water and providing desirable growth conditions for the seeds. FIGS. 1A-1C show an exemplary container 10 having lip 14, side walls 18, and floor 20. Container 10 can include internal supports 24 capable of suspending membrane 30 above floor 20. Internal supports 24 can include, for example, one or more ridges protruding up from floor 20 and/or a ledge projecting inward from sidewalls 18 to support membrane 30 above floor 20. A lid may be used to cover container 10. A lid may be unattached to container 10 or it may be attached to container 10 at one edge of lip 14. When a lid is placed over container 10, container 10 is closed. In one embodiment, container 10 covered with a lid is air permeable. The seal formed from covering container 10 with a lid is not an air-tight seal.

Containers for the cryo-sprouts described herein can be containers such as "clam shell" containers or other plastic or polymer based packages. Preferably, the container is made from materials that do not absorb water and are not compromised, i.e. softened, by exposure to water. Containers can also be glass, ceramic, plastic tubs with lids and growing trays with lids. Containers made from other suitable materials are also within the scope of this disclosure. In one embodiment, containers may be single use containers. In one embodiment, the container may be a larger container and the cryo-sprouts can be harvested from the larger container. The larger container may be, optionally, cleaned and reused.

In various embodiments, containers can include internal supports configured to suspend a membrane above the floor of the container. The internal supports can be ridges projecting upwards along the length or the width of the floor as exemplified in FIGS. 1A-1C. The internal supports can also be finger like projections projecting upwards from the floor of the container. The internal supports may also include a ledge projecting inward from the bottom of at least two of the sidewalls of the container. Preferably, the internal supports in the container are configured to suspend the membrane above the floor of the container while providing sufficient volume below the suspended membrane for addition of the desired amount of water. Desirable amounts of water can vary and are discussed herein. A lid configured to close the container may also be included.

Membranes used in the trays can be made from a variety of materials and can vary in size. Generally the membranes are sized to fit the interior dimensions of the trays. In various embodiments, there is not a sufficient gap between the edges of the membrane and the sidewalls of the trays for the seeds to fall off the membrane and onto the floor of the tray. The membranes can be made of woven or non-woven material. In one embodiment, the membrane includes non-woven material. Materials for the membrane can include polyester, polypropylene, nylon filaments and the like. In one embodiment, the membranes are non-hygroscopic. The membrane can include a single material or a laminate. In one embodiment, the membrane is a polypropylene fiber membrane UNIPRO200FX purchased from MIDWEST FILTRATION®, LLC. Cincinnati, Ohio. In one embodiment, the membrane is sufficiently strong to support the seeds. In various embodiments, the membrane can allow water to permeate through the membrane to the floor of the container. In one embodiment, the water can permeate the membrane at a rate that can facilitate uniform seed dispersion.

Figure 2:
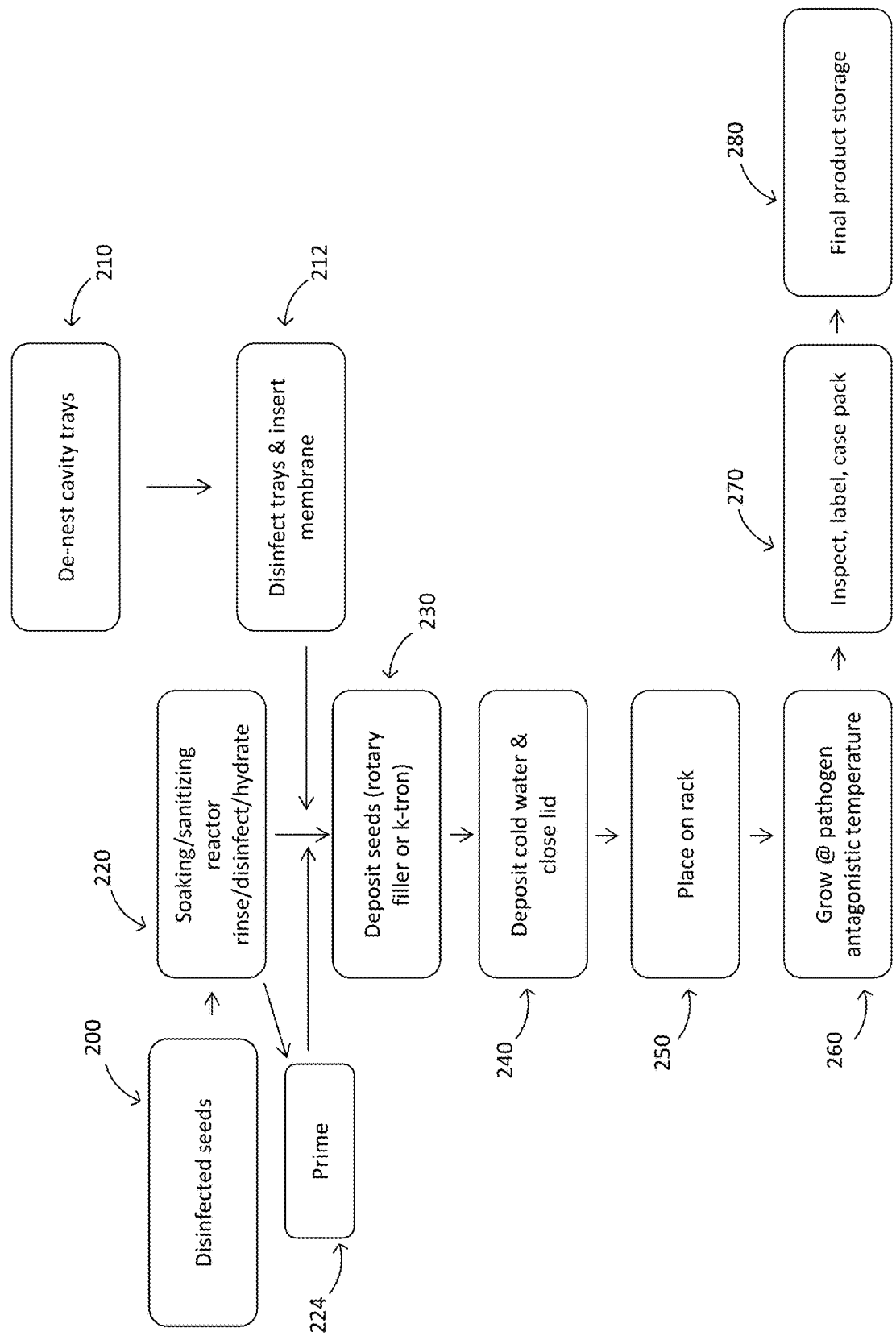
FIG. 2 is a flow diagram of an exemplary process for growing cryo-sprouts.
Figure 3A:
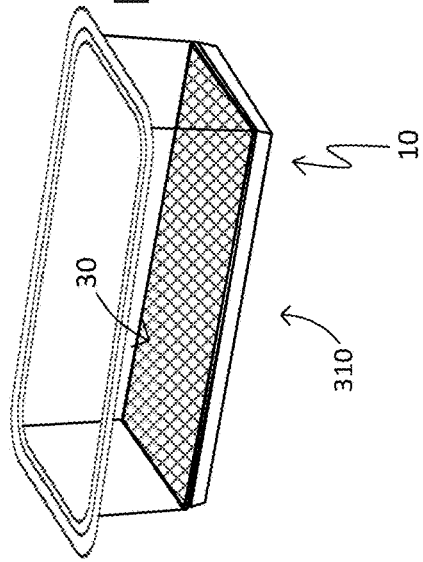
FIGS. 3A-3F are schematics of a flow diagram of an exemplary process for growing cryo-sprouts.
Figure 3B:
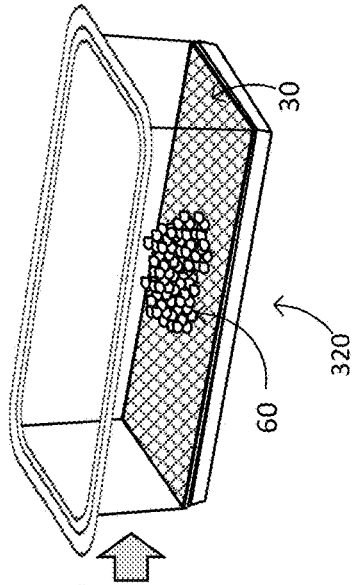
Figure 3C:
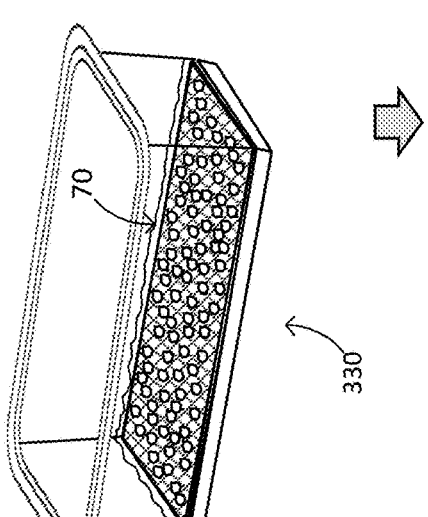
Figure 3D:
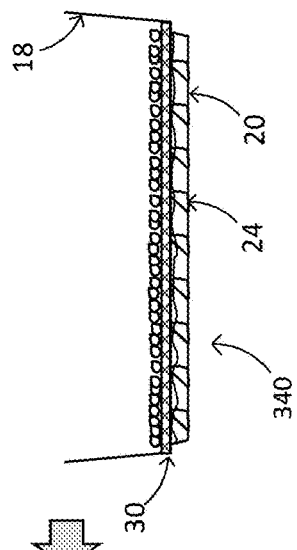
Figure 3E:
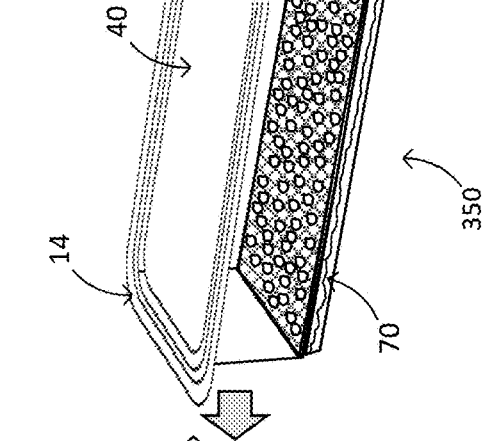
Figure 3F:
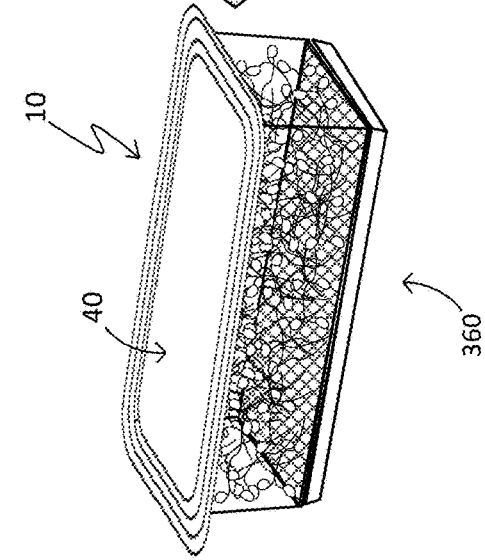
Figure 5A:
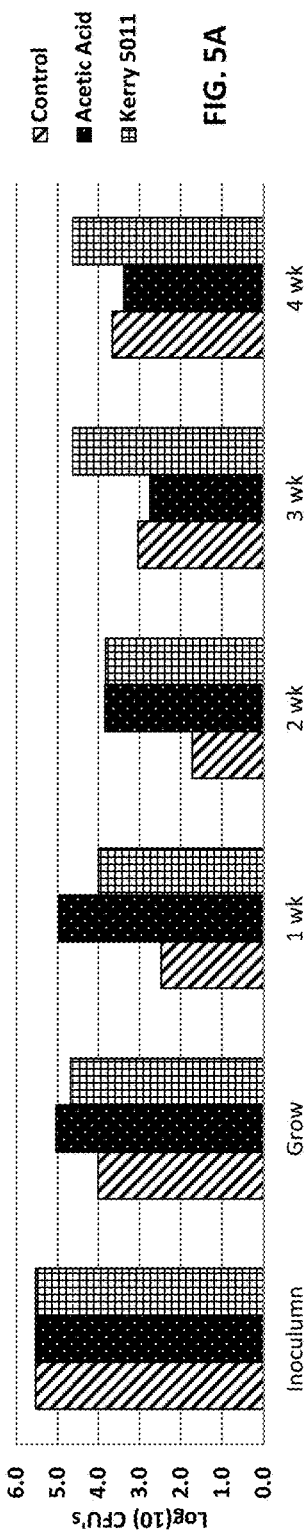
FIGS. 5A-5C are bar graphs of the effect of seed hydration on growth of sprouts at 50° F. for *E. coli* O157:H7, *Salmonella* and *Listeria*, respectively.
Figure 5B:
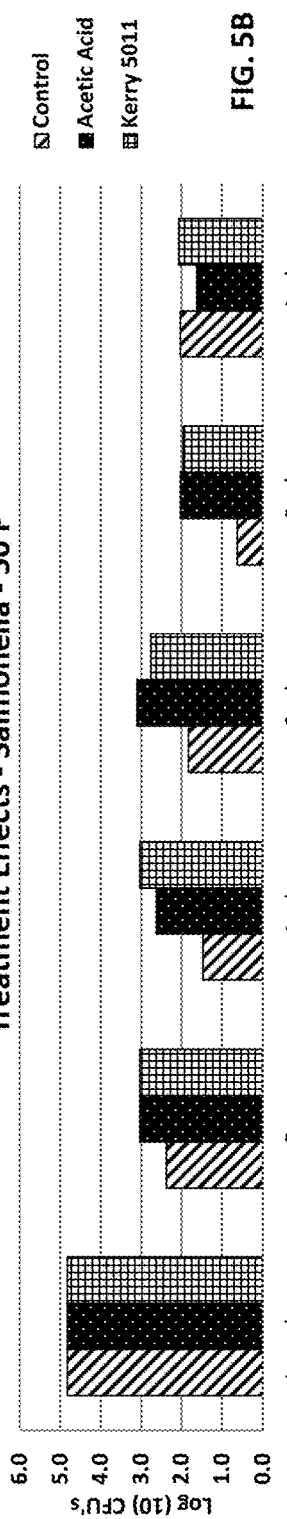
Figure 5C:
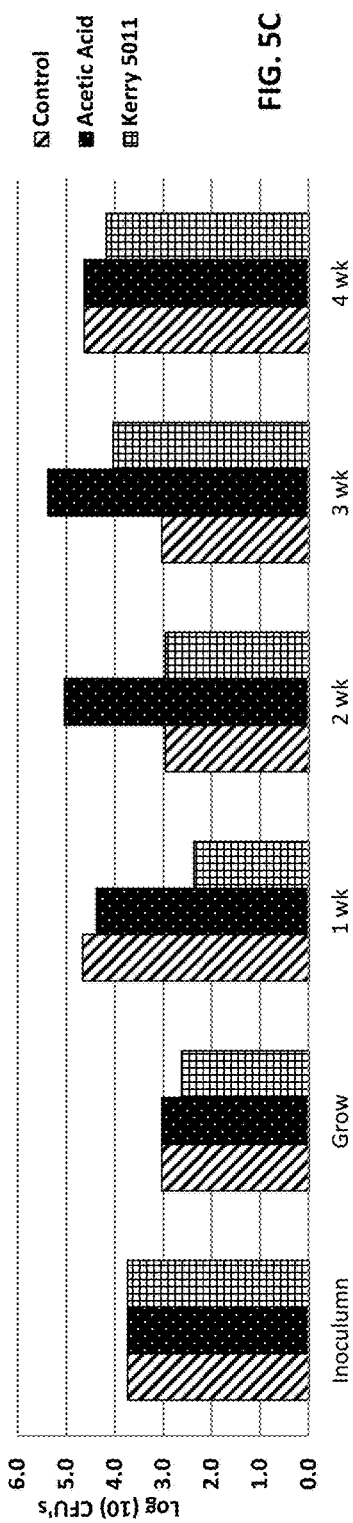

FIG. 2 shows a flow diagram of the steps included in an exemplary process of growing cryo-sprouts. Seeds are obtained from distributor (200) and transferred to a soaking/sanitizing reactor (220) where they are rinsed, further disinfected and hydrated. Reactor (220) can be obtained, for example, from FARMTEK®, Dyersville, Iowa.

Disinfection of seeds may be conducted using a variety of methods. Methods of disinfection can include, for example, chemical processing, high pressure processing, UV light and ionizing irradiation. Disinfection also may be performed, for example, using sodium hypochlorite. In an exemplary embodiment, seeds are disinfected in sodium hypochlorite at about 2000 ppm, buffered to pH 6.0 with acetic acid, for about 10 to about 15 minutes. Other methods of disinfection using other disinfectants, at different concentrations for varying amounts of time are all within the scope of this invention. Disinfection may be performed before, after or concomitant with hydration.

Hydration of the seeds can be performed by submerging the seeds with an excess amount of water or other hydrating composition and the time of hydration can be used to control the amount of liquid uptake. The seeds may be hydrated, for example, between about 60 minutes and about 180 minutes. Hydration times below 60 minutes and greater than 80 minutes are also within the scope of this invention. In an exemplary embodiment, about one gram of water is used per gram of air-dried seeds for hydration. Amount of water for hydration greater than about 1 gram of water per gram of air-dried seeds or less than about 1 gram of water per gram of air-dried seeds is also within the scope of the invention. The temperature of the water for hydration can vary and can be, for example, between about 4° C. and about 35° C.

During hydration, the seeds are preferably gently moved or stirred to maximize the exposure of the surface area of the seeds to the water. Moving or stirring of the seed/water mixture is preferably performed without damage to the seed.

Varying hydrating compositions can be used to hydrate the seeds. In one embodiment, water can be used for hydration of seeds as described above. Hydration may also be performed in other liquids, for example, a diluted solution of cranberry and/or carrot juice, liquids with acetic acid, acidic broths such as a Kerry acid 5924 and the like. Acetic acid can be, for example, between about 0.01% w/w and about 1% w/w.

In various embodiments, hydrating composition may include other components added to water or other liquids and used for hydration of seeds as disclosed above. In one embodiment, the hydrating composition can include a fermentate. In one embodiment, the hydrating composition can include a fermentate derived from lactic acid fermenting bacteria, for example, *Lactobacillus casei, Lactococcus lactis* and the like. Fermentate from other lactic acid bacteria may also be used and these fermentates are within the scope of this description. In one embodiment, the fermentate can include bacteriocin(s), e.g. nisin, as one of the fermentate products. Other components that can be included in the hydrating compositions include, for example, nisin, cranberry juice, benzoic acid and other phenolic compounds and the like. A combination of one or more of these components may also be included in the hydrating composition. In one embodiment, the hydrating composition includes bacteriocin(s) added to water.

In various embodiments, the amount of the fermentate that can be included in the hydrating composition can be between about 0.1 percent by weight and about 5 percent by weight, such as between about 0.25 percent and about 1 percent by weight. In one embodiment, the hydration of the seeds is performed in a composition that includes about 0.5% of Kerry 5924 by weight.

In various embodiments, after hydration (220), the seeds may, optionally, be primed (224). In one embodiment, the priming is performed after hydration (220) but prior to planting or initiation of the growth phase. In other words, the priming is performed prior to deposition of seeds onto membranes of individual trays (230) and addition of the total amount of water needed for growth of the cryo-sprouts. Priming may also be performed after placement into individual trays but prior to addition of the total amount of water needed for the growth of the cryo-sprouts.

Priming (224) can include storing the hydrated seeds in large containers or trays. These can be the large containers and trays in which hydration of the seeds was conducted. In various embodiments, priming can include storing the hydrated seeds in minimal or no light for a period of time. In one embodiment, the hydrated seeds are stored in the dark. Priming (224) can be performed at various temperatures including at a pathogen antagonistic temperature. Priming (224) can be performed at temperatures between about 35° F. and about 45° F. In one embodiment, priming (224) was performed at a temperature between about 38° F. and about 42° F.

The seed depth during priming (224) can vary and all are within the scope of this disclosure. In various embodiments, the seed depth can be between about one inch and about five inches. In one embodiment, the seed depth is between about one inch and about 3 inches such as about 1.5 inches. Seed depths outside of this range are also within the scope of this disclosure.

The duration of priming (224) can vary and can be dependent on, for example, the specific seeds, the age of the seeds, the moisture content of the seeds and the like. If the seeds are primed, priming (224) may be for at least a day. In one embodiment, priming (224) may be for at least a week, such as for at least about two weeks to at least about 3 weeks. Priming (224) for longer than about 3 weeks is also within the scope of this disclosure.

The desirable length of priming can vary for each seed type. If the priming period is carried out for too long, it may have a deleterious effect for some of the seeds. A desirable length of priming for some seeds, e.g. broccoli, may be too long for other seeds, e.g. clover. In various embodiments, priming for an extended period of time may reduce the percentage of germination of the planted seeds. In other words, seeds are susceptible to being over-primed. The ideal length of priming for each seed can vary.

In one embodiment, priming (224) of the seeds is not necessary and hydrated seeds (220) can be planted by depositing (230) the desired number of seeds in the individual containers and water added (240) for germination and growth of the seeds into cryo-sprouts. Seeds that may not require priming include, for example, alfalfa, clover, cress and the like.

In various embodiments, priming (224) may not be necessary but can enhance growth of the cryo-sprouts by reducing the growth period at the pathogen antagonistic temperature. The seeds, for example, may need about 21 days from planting to grow into cryo-sprouts. However, priming the seeds prior to planting as disclosed above, can reduce the time from planting to growth into cryo-sprouts. Priming may reduce the growth period, for example, by about several days and/or about 1 weeks to about 2 weeks. Seeds that have an enhanced growth profile by priming prior to planting include, for example, alfalfa, kale, clover, radish, broccoli and the like In various embodiments, seeds may be recalcitrant to growth of cryo-sprouts without the inclusion of priming prior to planting. In these seeds, priming can be performed prior to planting for at least some duration as disclosed above. Seeds that are greatly enhanced by priming or recalcitrant to growth without priming include, for example, broccoli, some varieties of kale, some varieties of radish and the like.

It can be particularly advantageous to perform the priming in large containers or trays prior to separation into trays where the cryo-sprouts can be grown as this can be efficient use of manufacturing space. The containers with the seeds during priming can have vents in the trays for respiration. The containers with the seeds during priming may also include membranes disclosed herein.

Cavity trays may be de-nested (210), if necessary. After de-nesting, the trays can be disinfected and the membranes can be placed in the cavity of the trays (212). Trays may be disinfected using a variety of methods known in the art and may include sanitization using hydrogen peroxide, alcohol, ultraviolet light, steam or other appropriate sanitizing agents. Trays may also be used without any further sanitizing procedure. Trays formed using high temperatures may be "commercially sterile" and can be used directly without further disinfection.

The hydrated seeds can be deposited on the membrane in the disinfected tray (230). A variety of methods can be used to deposit the seeds in the tray including, for example, a rotary filler such as the K-tron gravimetric feeder purchased from COPERION K-TRON®, Sewell, N.J. The amount of seeds deposited in each tray can vary depending on the size of the tray and the desired amount of cryo-sprouts in each tray.

Water can be added to the seeds (240) in the tray and covered with a lid. Generally, the water permeates the membrane at a rate that facilitates seed dispersion across the membrane. In other words, the amount of water and the rate of water permeation through the membrane preferably allows for the water to pool above the membrane sufficiently to disperse the seeds across the membrane before flowing through the membrane and leaving a dispersed seed layer or layers. The membrane with the dispersed seeds can be held above the floor of the container by the internal supports. The membrane with the dispersed seeds may rest at the surface of the water or slightly above or slightly below the surface of the water. The seeds after dispersion may be in a single layer. Alternatively, there may be more than one layer of seeds. Surprisingly, assimilation of the water by the seeds has been found to occur even without direct contact with the added water at the bottom of the container. Without being bound to any theory, the water in the container may be transported via vapor phase to the seeds that are not directly in contact with the water below the membrane. This can enable the assimilation of the water by the seeds when not in direct contact with the water below the membrane. Assimilation as used herein refers to use and/or incorporation of the water by the seeds for growth.

The trays may be placed on racks (250) and/or carts for stable movement into the growth chamber. If a large storage room is used for the growth phase, for example, multiple trays may be placed on a rack and transferred to a cart that can then be wheeled into a growth chamber. The trays may be moved using any convenient method for moving trays containing water without spillage of water or without substantially disturbing the dispersion of the seeds on the membrane.

The covered trays with the seeds dispersed on the membrane and water are generally incubated (260) at a pathogen antagonistic temperature during the growth period. The covered trays with the seeds may also be exposed to light. In one embodiment, the covered trays are exposed to light for the entire growth period. In one embodiment, the covered trays are in the dark for an initial portion of the growth period such as for about 2 to about 8 days and then exposed to light. The amount of light provided can vary. Room light or office light may be sufficient for the germination of the seeds and growth of the sprouts. Exposure to light that is more or less than office lighting is also within the scope of the description. The cryo-sprouts are generally above the membrane and the root system of the cryo-sprouts generally does not penetrate through the membrane but stays above or interwoven through the mesh of the membrane. After growth of the cryo-sprouts, the trays may be inspected, labeled and further packaged, if desired (270). The final product can then be stored (280) until consumption. The cryo-sprouts may also be transferred to a different container or a bag.

FIG. 3 shows a schematic flow diagram using an exemplary process with a cavity tray for growing cryo-sprouts. The labeled container components are consistent with the labels in the container of FIGS. 1A-1C. The process includes container 10, with membrane 30, floor 20 and internal supports 24 (310). Seeds 60 are placed on membrane 30 (320). Water 70 has been added to container 10 (330). Water 70 permeates through membrane 30 at a rate that can facilitate the dispersal of seeds 60. A side view of container 10 (340) shows membrane 30 supported on internal supports 24. The membrane can be resting approximately at the surface of water 70. Alternatively, the membrane can be slightly above the surface of the water or slightly below the water surface without having the seeds totally submerged. Lid 40 is added to close the container (350) and stored at a pathogen antagonistic temperature. The cryo-sprouts can grow at the pathogen antagonistic temperature (360) after a sufficient growth period.

The amount of seeds placed in the container can be dependent on the size of the container used and the size of the sprout product desirable to be offered to the consumer. Any amount of seeds may be used and all are within the scope of this disclosure.

The amount of water added to the seeds at the initiation of the growth period or at the time of planting can vary and be dependent on the size of the container, the type of internal supports and the amount of seeds. The water may be passed through a filter before use, e.g., about a 0.45 micron filter. Filters of other sizes may also be used and are within the scope of this description. Preferably, all of the water needed by the seeds for growth into cryo-sprouts is included in the container before a lid is placed over the container.

Internal supports within the container are preferably configured to accommodate the desired amount of water without submersion of the seeds on the membrane. In an exemplary embodiment, the seeds dispersed on the membrane have contact with the water surface initially. In another exemplary embodiment, the dispersed seeds are in more than one layer, i.e. resting on other seeds and not directly on the membrane such that all the seeds may not be in contact with the added water. For example, the membrane with the dispersed seeds may float on the water surface or the water may be sufficient to partially, but not completely, submerge the seeds dispersed on the membrane.

The seeds can assimilate water by direct contact with the water and also by contact with the water in the vapor phase in the container. Assimilation of the water by the seeds can result in the reduction of the water level in the container during the growth period. Generally, the water in the container enters the vapor phase prior to the cryo-sprouts becoming fully grown. As germination and growth proceed, the seeds dispersed on the membrane maintain less contact with the water at the bottom of the container and more water contact through the water transported into the vapor phase. The water in the container can be absorbed by the seeds or enter the vapor phase in about 3 days to about 15 days. In an exemplary embodiment, the water in the container is absorbed by the seeds or enters into the vapor phase between about 4 days and about 8 days. When the water is absorbed or assimilated by the seeds or enters the vapor phase, then very little to no water is remaining at the bottom of the container. However, growth of the sprouts can continue using the assimilated water and/or water transported into the vapor phase. Once this occurs, the membrane generally rests on the internal supports.

The amount of water added per gram of air dry seeds can vary and may be dependent on a number of factors including the variety of seed. The amount of water added can also be dependent, for example, on the amount of water provided during hydration of the seeds. Water for assimilation by the seeds can be provided during the hydration step and also added to the container at the time of planting or prior to incubation at the pathogen antagonistic temperature. The amount of water per gram of air dried seeds can be between about 2 grams water per gram of air dry seeds and about 10 grams water per gram of air dry seeds, preferably between about 3 grams water and about 6 grams per gram of air dry seeds, and more preferably between about 4 grams water and about 5 grams water per gram of air dry seeds. These ranges include water absorbed by the seeds during hydration and water provided in the container. Amount of water per gram of air dry seeds outside of these ranges are also within the scope of this description.

The trays with the seeds, water and membrane can have a growth phase and a storage phase. The growth phase generally begins after planting when the trays are incubated at a pathogen antagonistic temperature in a growth chamber (after addition of seeds, water and lid). The growth phase can be characterized by a period when the seeds in the container are assimilating the water in the container and when germination and the growth of the seed radicle occurs. By the end of the growth phase, the water has been assimilated into the cryo-sprouts. In an exemplary embodiment, by the end of growth phase, sprouts can fill a package when about 17.5 grams of air dried seeds are in containers with about 500 cm$^3$ of volume. This is merely illustrative and not limiting and other seed amounts and volume of containers are all within the scope of the description. The growth chamber can be a walk-in room maintained at the desired conditions. It may also be an appliance such as a refrigerator that can maintain the desired conditions.

The storage phase may also be referred to herein as shelf-life and can begin when the growth of the cryo-sprouts is substantially complete. During the storage phase, the sprouts can be in stasis and the assimilation of water by the seeds is substantially complete. The sprouts are alive and respiring during the storage phase and this respiration can occur using the water present in the sprouts, i.e. already assimilated by the seeds for growth into sprouts. The sprouts, for example, during the storage phase may become greener due to the continued respiration of the sprout. The storage phase or the shelf-life can end when the cryo-sprouts no longer have desirable attributes for consumption. This generally occurs when the sprouts cease respiration generally due to diminished resources. Shelf-life begins at about the end of growth phase and ends at about the time when the cryo-sprouts no longer are consumable.

Sprouts are susceptible to harboring a variety of microorganisms. These microorganisms can be present on seeds, in the water, in containers, in the air and the like. Sanitization protocols may reduce the number of microorganisms, however they generally do not remove all of the microorganisms if the seeds are still viable. Furthermore, the conditions normally used for growth of the sprouts are also conducive to the growth of microorganisms. The microorganisms harbored in sprouts can include pathogenic as well as non-pathogenic microorganisms. Non-pathogenic bacteria do not harm the consumer upon consumption of the sprouts. Pathogenic organisms can sometimes become virulent and be harmful to the consumer.

The growth and quality of sprouts can be dependent on a number of conditions including temperature, light, water and the like. The method of growing cryo-sprouts described herein can include incubating the trays at a pathogen antagonistic temperature during the growth phase. At the pathogen antagonistic temperature, the growth or number of targeted pathogens such as *Salmonella* and *E. coli* are reduced or eliminated. At the pathogen antagonistic temperature, the number of some targeted pathogens such as *Listeria* is maintained at about the same amount. Preferably, the targeted pathogens are not increasing in number. Thus, the pathogen antagonistic temperature can act as a microbicidal agent or a microbiostatic agent with respect to the undesirable pathogens in cryo-sprouts grown in trays according to methods described herein.

"Microbicidal" as referred to herein relates to an agent or conditions that decrease the number of microbes such as bacteria. "Microbiostatic" as referred to herein relates to an agent or conditions that maintain the number of microbes such as bacteria.

The covered trays with the seeds dispersed on the membrane and water are generally incubated at a pathogen antagonistic temperature for growth. This is in direct contrast to the prior art methods that generally grow the sprouts in ambient temperature of about 68-70° F. or higher. The pathogen antagonistic temperature is preferably between about 35° F. and about 45° F., more preferably between about 38° F. and about 42° F.

The container including the seeds, the membrane and the water can be incubated for varying amounts of time for the growth of the cryo-sprouts and will be referred to herein as the growth period or growth phase. When the container is incubated at a pathogen antagonistic temperature, the growth period can be at least about 14 days, and in some embodiments the growth period can be at least about 20 days. In an exemplary embodiment, the growth period at a pathogen antagonistic temperature of about 40° F. can be about 21 days. Growth periods of longer than 21 days are also within the scope of this disclosure.

In various embodiments, growth of the cryo-sprouts in the container may be enhanced by exposure to a desirable amount of light or illumination. The amount of light provided can generally be between about 0 lux and about 5000 lux. Preferably, the amount of light provided is between about 10 lux and about 1000 lux. More preferably, the amount of light is between about 20 lux and 500 lux. Values outside of these ranges are also within the scope of the present disclosure.

In various embodiments, at least about 50 percent, such as at least about 80 percent of the seeds in the container are germinated. In one embodiment, at least about 90 percent of the seeds in the container are germinated. In another embodiment, at least about 95 percent of the seeds in the container are germinated.

Figure 6A:
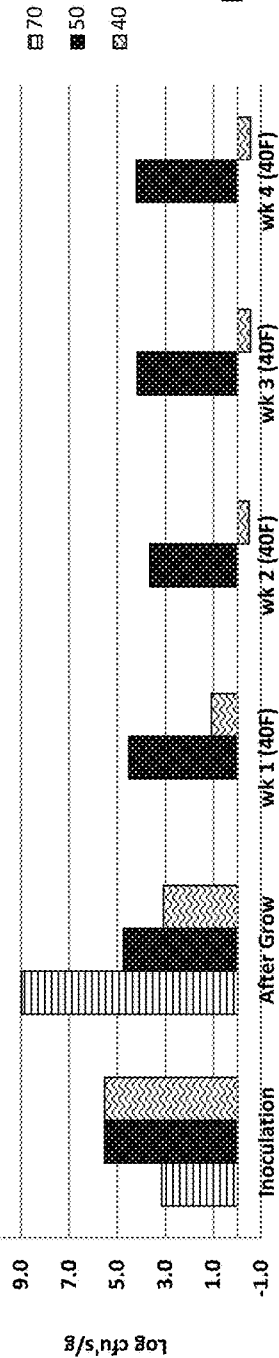
FIGS. 6A-6C are bar graphs of the effect of temperature on growth of *E. coli* O157:H7, *Salmonella* and *Listeria*, respectively is sprouts.
Figure 6B:
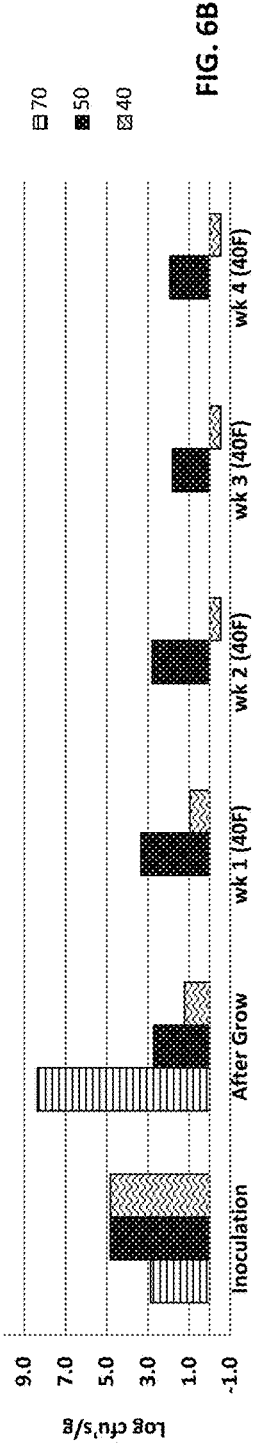
Figure 6C:
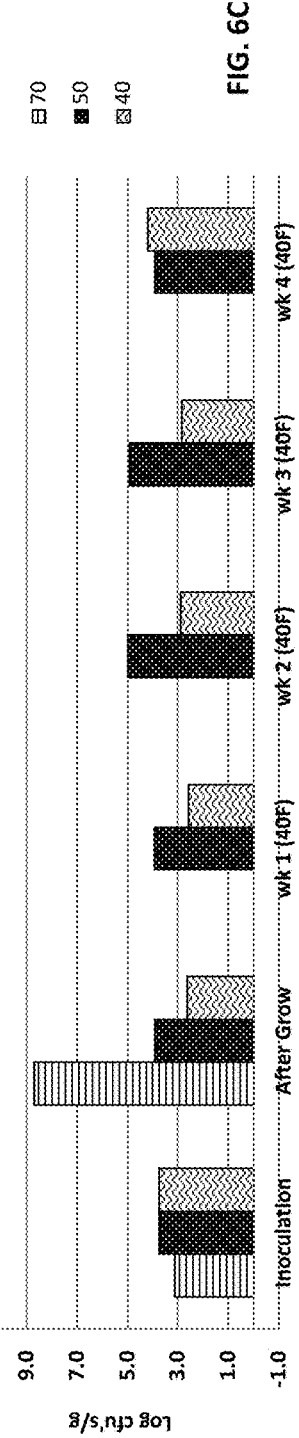

A variety of pathogenic bacteria can be targeted for reduction or elimination by growing cryo-sprouts at a pathogen antagonistic temperature. The pathogenic bacteria can include, for example, *Escherichia coli* O157:H7, *Salmonella* spp., and *Listeria* and the like. In some exemplary embodiments, growth of *E. coli* and *Salmonella* can be reduced during the growth of the cryo-sprouts, i.e. the growth period and also during the shelf-life. In other exemplary embodiments, the number of *Listeria* bacteria, for example, can be static or roughly equivalent to the number of *Listeria* at the beginning of the growth period. FIGS. 4A-4B and FIGS. 6A-6B show that the number of *Escherichia coli* O157:H7, *Salmonella* spp., decrease in number from the inoculum added at the beginning of the growth stage and by the end of the growth phase when incubated at a pathogen antagonistic temperature of about 40° F. These figures also indicate that the number of pathogens are decreased during the storage of the cryo-sprouts, i.e. during the shelf life. FIG. 4C and FIG. 6C show that the number of *Listeria* do not increase when a pathogen antagonistic temperature of about 40° F. is used. FIGS. 5A-5C and FIGS. 6A-6C indicate that when the cryo-sprouts are grown at a temperature of about 50° F. or about 70° F. the numbers of pathogens are significantly higher. In FIGS. 4A-4C and FIGS. 5A-5C, the control treatment is hydration of the seeds in water.

Although the number of pathogenic bacteria can be reduced, eliminated or maintained at a static level during the growth period, the number of total bacteria at the end of the growth stage of the cryo-sprouts and/or the storage phase may be similar to the total number of bacteria in a container of cryo-sprouts grown at 50° F. or higher. In other words, a container of cryo-sprouts grown using the methods described herein may have similar number of total bacteria relative to a container of sprouts grown at ambient temperature. However, the total number of bacteria can have reduced number of pathogens. In other words, the cryo-sprouts can have no or a significantly reduced numbers of pathogenic bacteria.

After the growth of the cryo-sprouts, the cryo-sprouts may be stored at a storage temperature. Preferably, the storage temperature is at about the pathogen antagonistic temperature or slightly below the pathogen antagonistic temperature. In some exemplary embodiments, the storage temperature is between about 32° F. and about 45° F. In some preferred embodiments, the storage temperature is between about 35° F. and about 42° F. Storage temperatures may be outside of this range and are also within the scope of this disclosure. The sprouts may be transported during the storage phase. Transport of the sprouts during the growth phase is also within the scope of this description.

The cryo-sprouts grown by the methods disclosed herein can have an extended shelf-life. The shelf-life or the storage phase of the cryo-sprouts described herein can be at least about 15 days, preferably the shelf-life of the cryo-sprouts is at least about 21 days and more preferably the shelf-life is at least about 28 days. The shelf-life may vary depending on the specific type of cryo-sprouts in the container, the storage temperature, the number of spoilage bacteria and the like. In some exemplary embodiments, the shelf-life of the cryo-sprouts is about 28 days.

In one exemplary embodiment, about 35 grams of hydrated seeds (~17.5 grams air dry seed and 17.5 grams water) are added to a container. About 60 grams of cold water is added to the container. This is an exemplary ratio and other ratios are also within the scope of this disclosure. The container is closed and placed at a pathogen antagonistic temperature of about 40° F. and with an illumination of about 50 lux and grown for about 21 days. After about 21 days, the final product can be stored at a storage temperature of about 35-40° F. for an extended shelf-life of at least about 28 days. This is one exemplary embodiment, and variations in the amount of seeds, water, temperature, illumination, growth time and shelf-life are within the scope of this disclosure.

The present disclosure also includes a container that includes cryo-sprouts. The container can include cryo-sprouts grown from seeds, for example, of alfalfa, clover, kale, broccoli, radish, mustard, flax, green peas, onion, sunflower, corn, wheat, oats, barley, rye, soybeans, and the like. In some preferred embodiments, cryo-sprouts are grown from alfalfa, clover, kale and broccoli seeds. Initially, the container can include water, seeds, membrane and a lid or cover. The covered container is not air-tight but allows for permeation of air. As small percentage of the water in the container may be transported into a vapor phase in the container during the growth phase of the cryo-sprouts. The container with the cryo-sprouts at the end of growth phase generally includes minimal or no standing water.

The cryo-sprouts described herein have enhanced color characteristics. The cryo-sprouts can have a more vibrant green color and also retain the green color for a longer period of time.

The present disclosure can also include a method of providing cryo-sprouts to a consumer. The method can include growing cryo-sprouts from hydrated seeds in a container at a pathogen antagonistic temperature. The container can include a membrane supported on an internal support above the floor of the container. The pathogen antagonistic temperature can be between about 35° F. and about 45° F., preferably between about 38° F. and about 42° F. The shelf-life of the cryo-sprouts can be about at least about 21 days, preferably about 28 days or longer. The cryo-sprouts can be stored at the storage temperature of between about 35° F. and about 42° F.

The present disclosure can also include a method of reducing pathogenic bacteria in cryo-sprouts. The method can include growing cryo-sprouts from hydrated seeds in a container at a pathogen antagonistic temperature. The container can include a membrane supported on an internal support above the floor of the container. The pathogen antagonistic temperature can be between about 35° F. and about 45° F., preferably between about 38° F. and about 42° F. The shelf-life of the cryo-sprouts can be about at least about 21 days, preferably about 28 days or longer. The cryo-sprouts can be stored at the storage temperature of between about 35° F. and about 42° F.

EXAMPLES

Example 1

The growth of *Salmonella*, *Listeria monocytogenes*, and *E. coli* O157:H7 on cryo-sprouts was evaluated when subjected to treatment with acetic acid (0.6% DWV) and Kerry 5011 (0.25%) and subjected to two temperature treatments versus a control treatment exposed to the same temperatures.

Isolates used to inoculate cryo-sprouts were grown in pure culture and quantitated in order to determine dilutions required to achieve a target level when inoculated into the product. This target level greatly exceeds that which would be found in commercial practice, even with highly contaminated seeds.

The study encompassed three treatments exposed to two different temperatures over the course of 28 days, with weekly pulls, see Table 1 below.

TABLE 1

| Treatment | Temperature |
| --- | --- |
| No Soak Hurdle (Control) | Grown for 21 days at 40° F., then held at 40° F. till Day 28 |
| | Grown for 12 days at 50° F., then held at 40° F. till Day 28 |
| Acetic Acid (0.6% DWV*) | Grown for 21 days at 40° F., then held at 40° F. till Day 28 |
| | Grown for 12 days at 50° F., then held at 40° F. till Day 28 |
| Kerry 5011 (0.25%) | Grown for 21 days at 40° F., then held at 40° F. till Day 28 |
| | Grown for 12 days at 50° F., then held at 40° F. till Day 28 |

*Distilled White Vinegar

Initial counts were determined immediately after inoculation for each treatment on Day 0, and again after incubation at 40° F. for 21 days, and 50° F. for 12 days. Subsequent pulls occurred on a weekly basis from Day 0 (after the 21 days at 40° F. or after 12 days at 50° F.) through Day 28. The pulls occurred on Shelf Life Day 0, 7, 14, 21, and 28.

Challenge Organisms

The *Salmonella* spp., *L. monocytogenes*, and *E. coli* O157:H7 cultures employed in this study were selected from the DEIBEL LABORATORIES CULTURE COLLECTION of Madison, Wis., as well as the DEIBEL LABORATORIES CULTURE COLLECTION of Gainesville, Fla.

TABLE 2

| *Salmonella* spp. Cultures | *L. monocytogenes* Cultures | *E. coli* O157:H7 Cultures |
| --- | --- | --- |
| *S. Bredeney* 10728 | *L. monocytogenes* WP986C | *E. coli* O157:H7 ATCC# 35150 |
| *S. Senftenberg* | *L. monocytogenes* FSIS 163 | *E. coli* O157:H7 FSIS 064-93 |
| *S. Newport* | *L. monocytogenes* ATCC# 15313 | *E. coli* O157:H7 FSIS 063-93 |
| *S. Enteritidis* GFP-108 | *L. monocytogenes* ATCC# 19115 | *E. coli* O157:H7 GFP-85 |
| *S. Cubana* | *L. monocytogenes* ATCC# 19111 | |

Methodology

Culture Preparation: One milliliter from each of the five *Salmonella* cultures was combined to form a cocktail. The *Listeria monocytogenes* and *E. coli* O157:H7 cultures were similarly combined to form a second and third cocktail. See Table 2 above. These three cocktails were diluted and added to the trays containing 60 ml of deionized water.

Inoculation procedure: Plastic trays with membrane were filled with 35 grams of soaked sprout seeds representing each of the three treatment groups.

Sixty milliliters of deionized water was added to each tray along with a final concentration of approximately 1.0 E+3-1.0 E+4 cfu/ml of each of the three cocktails (*Salmonella* and *Listeria* together in one set, and *E. coli* O157:H7 into another set).

Dilution and Plating Procedure: Samples were plated after undergoing various treatments via the following procedure:

*Salmonella* samples were serially diluted and spread plated on a Tryptic Soy Agar (TSA) basal layer and capped with XLD, incubated at 95° F. (35° C.) for 2 days. An MPN (Most probable number), consisting of a combination of the three samples, was also set up on each pull day due to the high number of other organisms present in the samples which obscured the direct counts.

*Listeria* samples were serially diluted and plated on a TSA basal layer and capped with Modified Oxford Medium (MOX), incubated at 95° F. (35° C.) for 2 days. An MPN, consisting of a combination of the three samples, was also set up on each pull day due to the high number of other organisms present in the samples which obscured the direct counts.

*E. coli* O157:H7 samples were serially diluted and plated on a TSA basal layer and capped with EMB, incubated at 95° F. (35° C.) for 2 days. An MPN, consisting of a combination of the three samples, was also set up on each pull day due to the high number of other organisms present in the samples which obscured the direct counts.

Aerobic Plate Counts were also analyzed at Shelf Life Day 28 on the samples grown at 40° F. by plating to Standard Methods Agar and incubated at 95° F. for 2 days to determine the total aerobic bacteria present in the samples.

Results and Discussion

Seeds exposed to two treatments (acetic acid, DWV 0.6%, and Kerry 5011 0.25%), as well as control samples were analyzed for the levels of *Salmonella*, *L. monocytogenes*, and *E. coli* O157:H7 present at Day 0 (immediately after inoculation) and again after the seeds had been incubated at 40° F. for 21 days, and 50° F. for 12 days, denoted as Shelf Life Day 0 in tables. Subsequent pulls were conducted in triplicate weekly through Day 28 (Week 4). Good sprout growth was noted for each of the treatments at both temperatures and the growth/appearance was denoted as normal at each pull date for each treatment at both temperatures.

TABLE 3

| Treatment | Salmonella (MPN/g) or (CFU) | $Log_{10}$ (Salmonella MPN/g) or (CFU) | L. monocytogenes (MPN/g) or (CFU) | $Log_{10}$ (L. monocytogenes MPN/g) or (CFU) | E. coli O157:H7 (MPN/mL) or (CFU) | $Log_{10}$ (E. coli O157:H7 MPN/g) or (CFU) |
|---|---|---|---|---|---|---|
| Inoculation Culture | 3,800,000 | 6.58 | 4,000,000 | 6.60 | 9,900,000 | 7.00 |
| Day 0 Inoculated Controls | 62,062 | 4.79 | 4,543 | 3.66 | 308,147 | 5.49 |
| Inoculated Control After 21 Days at 40° F., Shelf Life Day 0 at 40° F. | 43 | 1.63 | <30 | 0.95 | 74 | 1.87 |
| Shelf Life Day 7 at 40° F. | 11 | 1.04 | 1,100 | 3.04 | 4.3 | 0.63 |
| Shelf Life Day 14 at 40° F. | <0.3 | <−0.5 | 93 | 1.97 | 0.36 | 0.4 |
| Shelf Life Day 21 at 40° F. | <0.3 | <−0.5 | 1,100* | 3.04 | <0.3 | <−0.5 |
| Shelf Life Day 28 at 40° F. | <0.3 | <−0.5 | 46,000 | 4.66 | <0.3 | <−0.5 |

*Actual Count is Greater than 1,100

Table 3 details the results for the control seeds incubated at 40° F. for 21 days, then held at 40° F. through Shelf Life Day 28. The data shown is the average of runs performed in triplicate. The MPN's provided a better estimate of the levels of the pathogens present for those pulls.

The level of *Salmonella* spp. present declined throughout the course of the study and by Shelf Life Day 14 the count for the MPN was <0.3 MPN/g, however, low levels of *Salmonella* spp. were detected through Shelf Life Day 21 via direct plating. Both the MPN and the direct plate counts were <0.3 MPN/g, and <10 cfu/g on Shelf Life Day 28, for a total log reduction of 3.84 logs.

The level of *L. monocytogenes* present varied throughout the course of the study; however, there were either direct counts, or MPN counts detected on each of the pull days. The MPN's are a better approximation of the level due to high numbers of other organisms present in the samples, and at Shelf Life Day 28 the MPN/g was 46,000, a log increase of 1.01 logs from the Inoculated Controls.

The level of *E. coli* O157:H7 also declined throughout the course of the study and by Shelf Life Day 28 only one of the three samples had a direct count (10 cfu/g), resulting in an overall log reduction of 4.52 logs from Day 0, the MPN's showed a similar decline with a result of <0.3 MPN/g on Shelf Life Day 28, a log reduction of 4.54 logs from Day 0.

The Aerobic Plate Counts conducted on Shelf Life Day 28 resulted in a very high level of aerobic bacteria present in the samples, an average of 4.8 E+8 (avg. log value 8.68). The high level of organisms present could have contributed to some competitive inhibition of the pathogens inoculated onto the seeds.

TABLE 4

| Treatment | Salmonella (MPN/g) or (CFU) | $Log_{10}$ (Salmonella MPN/g) or (CFU) | L. monocytogenes (MPN/g) or (CFU) | $Log_{10}$ (L. monocytogenes MPN/g) or (CFU) | E. coli O157:H7 (MPN/ mL) or (CFU) | $Log_{10}$ (E. coli O157:H7 MPN/g) or (CFU) |
|---|---|---|---|---|---|---|
| Inoculation Culture | 3,800,000 | 6.58 | 4,000,000 | 6.60 | 9,900,000 | 7.00 |
| Day 0 Inoculated Controls | 65,912 | 4.82 | 647 | 2.81 | 128,906 | 5.11 |
| Inoculated Acetic (0.6% DWV) After 21 Days at 40° F., Shelf Life Day 0 at 40° F. | 150 | 2.18 | 230 | 2.36 | <30 | 0.95 |

TABLE 4-continued

| Treatment | Salmonella (MPN/g) or (CFU) | Log$_{10}$ (Salmonella MPN/g) or (CFU) | L. monocytogenes (MPN/g) or (CFU) | Log$_{10}$ (L. monocytogenes MPN/g) or (CFU) | E. coli O157:H7 (MPN/mL) or (CFU) | Log$_{10}$ (E. coli O157:H7 MPN/g) or (CFU) |
|---|---|---|---|---|---|---|
| Shelf Life Day 7 at 40° F. | 9.2 | 0.96 | 4.3 | 0.63 | 9.3 | 0.97 |
| Shelf Life Day 14 at 40° F. | <0.3 | <−0.5 | 1,100 *Actual Count is >1.1E+3 | 3.04 | 0.30 | −0.5 |
| Shelf Life Day 21 at 40° F. | <0.3 | <−0.5 | 930 | 2.97 | <0.3 | <−0.5 |
| Shelf Life Day 28 at 40° F. | <0.3 | <−0.5 | 1,100 *Actual Count is >1.1E+3 | 3.04 | <0.3 | <−0.5 |

Table 4 details the results for seeds exposed to Acetic Acid (0.6% DWV) incubated at 40° F. for 21 days, then held at 40° F. through Shelf Life Day 28. The direct plate counts for all three organisms were obscured by the heavy growth of other organisms present in all three samples after Shelf Life Day 0; therefore the MPN's provided a better estimate of the levels of the pathogens present for those pulls.

The levels of Salmonella spp. and E. coli O157:H7 both declined throughout the course of the study to levels that were below the detectable limit for both the direct plating (<10 cfu/g) as well as the MPN (<0.3 MPN/g), for overall log reductions of 3.87 logs and 4.16 logs respectively.

The levels of L. monocytogenes varied throughout the study; however, counts were detected by either direct plating or MPN at every pull. The direct plating resulted in counts that averaged approximately 4 logs on Shelf Life Day 14, 21, and 28 for log increases of 1.33, 1.23, and 1.69 logs respectively. The MPN method resulted in slightly lower counts than the direct plating method on Shelf Life Day 21, 2.97 logs vs. 4.04 logs. All the MPN tubes were positive for Shelf Life Day 28 sample (>1,100 MPN/g), indicating the direct count of 4.50 logs is a closer approximation of the actual level present.

The Aerobic Plate Count conducted on Shelf Life Day 28 also resulted in very high levels of aerobic bacteria present in the samples, an average of 8.1 E+8 cfu/g (avg. log value 8.91). The high level of organisms present could have contributed to some competitive inhibition of the pathogens inoculated onto the seeds.

Table 5 details the results for the seeds exposed to Kerry 5011 (0.25%) incubated at 40° F. for 21 days, then held at 40° F. through Shelf Life Day 28. The direct plate counts for all three organisms were obscured by the heavy growth of other organisms present in all three samples after Shelf Life Day 0; therefore the MPN's provided a better estimate of the levels of the pathogens present for those pulls.

The levels of Salmonella spp. and E. coli O157:H7 both declined throughout the course of the study to levels that were below the detectable limit for both the direct plating (<10 cfu/g) as well as the MPN (<0.3 MPN/g), for overall log reductions of 3.96 and 4.35 logs respectively for Shelf Life Day 21 and 28.

The levels of L. monocytogenes varied throughout the study; however, counts were detected by either the direct plating or MPN at each pull. The final pull on Shelf Life Day 28 resulted in an approximate log value of 2.75 (the actual count for replicate C was >25,000 cfu/g (>4.40 logs) for an overall log reduction of <0.13 logs. The final MPN result was also >1,100 MPN/g (>3.04 logs) for an overall log increase of >0.16 logs.

The Aerobic Plate Count conducted on Shelf Life Day 28 resulted in very high levels of aerobic bacteria present in the samples, an average of 6.1 E+8 cfu/g (avg. log value 8.79). The high level of organisms present could have contributed to some competitive inhibition, of the pathogens inoculated onto the seeds.

TABLE 5

| Treatment | Salmonella (MPN/g) or (CFU) | Log$_{10}$ (Salmonella MPN/g) or (CFU) | L. monocytogenes (MPN/g) or (CFU) | Log$_{10}$ (L. monocytogenes MPN/g) or (CFU) | E. coli O157:H7 (MPN/mL) or (CFU) | Log$_{10}$ (E. coli O157:H7 MPN/g) or (CFU) |
|---|---|---|---|---|---|---|
| Inoculation Culture | 3,800,000 | 6.58 | 4,000,000 | 6.60 | 9,900,000 | 7.00 |
| Day 0 Inoculated Controls | 80,804 | 4.91 | 758 | 2.88 | 199,633 | 5.30 |
| Inoculated Kerry 5011 (0.25%) After 21 Days at 40° F., Shelf Life Day 0 at 40° F. | 460 | 2.66 | <30 | <1.5 | 92 | 1.96 |
| Shelf Life Day 7 at 40° F. | 7.5 | 0.88 | 4.3 | 0.63 | 24 | 1.38 |
| Shelf Life Day 14 at 40° F. | <0.3 | <0.5 | 1,100 *Actual Count is >1.1E+3 | 3.04 | 0.36 | −.4 |
| Shelf Life Day 21 at 40° F. | <0.3 | <0.5 | 36 | 1.56 | <0.3 | <−0.5 |
| Shelf Life Day 28 at 40° F. | <0.3 | <0.5 | 1,100 *Actual Count is >1.1E+3 | 3.04 | <0.3 | <0.5 |

TABLE 6

| Treatment | Salmonella (MPN/g) or (CFU) | Log₁₀ (Salmonella MPN/g) or (CFU) | L. monocytogenes (MPN/g) or (CFU) | Log₁₀ (L. monocytogenes MPN/g) or (CFU) | E. coli O157:H7 (MPN/mL) or (CFU) | Log₁₀ (E. coli O157:H7 MPN/g) or (CFU) |
|---|---|---|---|---|---|---|
| Inoculation Culture | 3,800,000 | 6.58 | 4,000,000 | 6.60 | 9,900,000 | 7.00 |
| Day 0 Inoculated Controls | 62,062 | 4.79 | 4,543 | 3.66 | 308,147 | 5.49 |
| Inoculated Control After 12 Days at 50° F., Shelf Life Day 0 at 50° F. | 240 | 2.38 | 1,100 *Actual count is >1.1E+3 | 3.04 | 1,100 | 3.04 |
| Shelf Life Day 7 at 40° F. | <30 | <1.5 | 46,000 | 4.66 | 430 | 2.63 |
| Shelf Life Day 14 at 40° F. | 240 | 2.38 | 930 | 2.97 | 9.30 | 0.97 |
| Shelf Life Day 21 at 40° F. | 4.3 | 0.63 | 1,100* | 3.04 | 1,100 | 3.04 |
| Shelf Life Day 28 at 40° F. | 110 | 2.04 | 4,300 | 3.63 | 4,600 | 3.66 |

*Actual count is >1.1E+3

Table 6 details the results for the control seeds incubated at 50° F. for 12 days, then held at 40° F. through Shelf Life Day 28. The direct plate counts for all three organisms were obscured by the heavy growth of other organisms present in all three samples after Shelf Life Day 21; therefore the MPN's provided a better estimate of the levels of the pathogens present for these pulls.

The levels of *Salmonella* spp. present declined over the course of the study, with an overall log reduction of 2.75 logs at the Day 28 pull via the MPN method, however there was still an average of 2.04 logs (110 MPN/g) present at Day 28 via the MPN method and an average of 1.72 logs present via the direct plating method, which was likely lower due to the effects of the competitive micro flora present in the sample which obscured the counts. In contrast, the cryo-sprouts grown at 40° F. had levels of *Salmonella* spp. present that were below the detectable limit at Shelf Life Day 28 via direct plating as well as the MPN method.

The levels of *L. monocytogenes* present in the sample increased over the course of the study after initial decreases on Shelf Life Day 0, 7, and 14 via the direct plating method. The Shelf Life Day 21 pull resulted in an average log value of 4.16 via direct plating, a log increase of 1.66 logs from Day 14, and an overall log increase of 0.50 logs from Day 0; however, the counts were obscured by background flora, potentially causing an overestimation of the actual level present. The MPN method resulted in a count of >1,100 MPN/g for Shelf Life Day 21. The Shelf Life Day 28 direct plating counts were also obscured by background flora, which may have caused an overestimation of the actual levels present (avg. 6.5 logs, log increase of 2.84 logs from Day 0), as the MPN method resulted in a log value of 3.63 (4,300 MPN/g), an insignificant log reduction of 0.02 logs from the Inoculation Control. Comparatively, the cryo-sprouts grown at 40° F. had higher levels present at Shelf Life Day 28 via the MPN method (4.66 logs, 46,000 MPN/g)

The Levels of *E. coli* O157:H7 present in the samples decreased throughout the course of the study; however, there was still an average of 3.66 logs present at Shelf Life Day 28 (log reduction of 1.83 logs), whereas the cryo-sprouts incubated at 40° F. had an average log value of 0.97 at Shelf Life Day 28 via direct plating and 0.95 logs (<10 cfu/g) via MPN.

TABLE 7

| Treatment | Salmonella (MPN/g) or (CFU) | Log₁₀ (Salmonella MPN/g) or (CFU) | L. monocytogenes (MPN/g) or (CFU) | Log₁₀ (L. monocytogenes MPN/g) or (CFU) | E. coli O157:H7 (MPN/mL) or (CFU) | Log₁₀ (E. coli O157:H7 MPN/g) or (CFU) |
|---|---|---|---|---|---|---|
| Inoculation Culture | 3,800,000 | 6.58 | 4,000,000 | 6.60 | 9,900,000 | 7.00 |
| Day 0 Inoculated Controls | 65,912 | 4.82 | 647 | 2.81 | 128,906 | 5.11 |
| Inoculated Acetic (0.6% DWV) After 12 Days at 50° F., Shelf Life Day 0 at 40° F. | 1,100 | 3.04 | 1,100 *Actual count is >1.1E+3 | 3.04 | 1,100 | 3.04 |
| Shelf Life Day 7 at 40° F. | 430 | 2.63 | 24,000 | 4.38 | 110,000 | 5.04 |
| Shelf Life Day 14 at 40° F. | 290 | 2.46 | 110,000 *Actual count is >1.1E+5 | 5.04 | 46,000 | 4.66 |
| Shelf Life Day 21 at 40° F. | 110 | 2.04 | 240,000 | 5.38 | 930 | 2.97 |
| Shelf Life Day 28 at 40° F. | 43 | 1.63 | 43,000 | 4.63 | 2,400 | 3.38 |

Table 7 details the results for the seeds exposed to Acetic Acid (0.6% DWV), incubated at 50° F. for 12 days then held at 40° F. through Shelf Life Day 28. The direct plate counts for all three organisms were obscured by the heavy growth of other organisms present in all three samples on Shelf Life Day 28; therefore the MPN's provided a better estimate of the levels of the pathogens present for that pull.

The levels of *Salmonella* spp. present declined throughout the course of the study; however there was still an average of 1.63 logs (43 MPN/g) present via the MPN method at Shelf Life Day 28. There were counts at each pull date ranging from 1.4-3 logs via MPN and plating methods, whereas the cryo-sprouts incubated at 40° F. had counts that were below the detectable limit for both the MPN and direct plating methods after Shelf Life Day 14.

The levels of *L. monocytogenes* increased by approximately 2.5 logs through Shelf Life Day 21 to an average of 5.31 logs (2.1 E+5 cfu/g) and 5.38 logs (2.4 E+5 MPN/g) via the direct plating and MPN methods respectively. The direct counts were obscured by background flora on Shelf Life Day 28, which may have caused an overestimation of the levels present (avg. log value of 7.95) as the MPN method resulted in a log value of 4.63 for an overall log increase of 1.82 logs from the inoculated controls. Here again the cryo-sprouts incubated at 40° F. while still showing a log increase over the course of the study it was smaller than the increase seen for the sprouts incubated at 50° F., 1.69 logs vs. 5.14 logs for the direct plating method and >0.23 logs vs. 1.82 logs for the MPN method.

The levels of *E. coli* O157:H7 decreased throughout the course of the study; however, there were substantial levels still present at each of the pull days. Overall, the log reduction at Shelf life Day 28 was 1.73 logs (avg. log value 3.38, 2,400 MPN/g) from the Day 0 inoculated control level via the MPN method. The counts for each pull day resulted in avg. log values ranging from approx. 3-5 logs, whereas, the cryo-sprouts incubated at 40° F. resulted in levels that ranged from approx. 1 log to 2 logs and were below the limit of detection via direct plating and MPN by the Shelf Life Day 21 pull.

other organisms present in all three samples on Shelf Life Days 21 and 28; therefore the MPN's provided a better estimate of the levels of the pathogens present for those pulls.

The levels of *Salmonella* spp. present declined throughout the course of the study; however, counts were above the detectable level through Shelf Life Day 28 via the direct plating and MPN methods. At Shelf Life Day 28 the MPN method resulted in a log value of 2.08 (120 MPN/g) for an overall log reduction of 2.83 logs from the Day 0 inoculated controls. The plate counts for Shelf Life Day 21 and 28 were slightly lower than the MPN method, 1.24 and 1.69 logs respectively, which was probably due to the large number of background flora present in the samples which obscured the counts. The cryo-sprouts incubated at 40° F., however, resulted in a nearly 4 log reduction by Shelf Life Day 14, with both the direct plate and MPN methods resulting in counts below the detectable limits from that point forward.

The levels of *L. monocytogenes* present in the samples increased over the course of the study with an overall log increase of 1.30 via the MPN method. The results of the direct counts for Day 28 were significantly higher with an avg. log value of 7.51 (3.2 E+8 cfu/g, log increase of 4.63 logs), however, large numbers of background flora may have caused an overestimation of the count. The seeds incubated at 40° F. also resulted in a net log increase via the MPN method; however, the increase was slightly lower than that of the seeds incubated at 50° F. (4.18 logs vs. >3.04 logs).

The levels of *E. coli* O157:H7 present in the samples declined over the course of the study; however, there were still significant numbers present at each pull. The Shelf Life Day 28 pull resulted in an avg. log value of 4.63 via the MPN method, and 3.92 for the direct plate method, for overall log reductions of 0.67, and 1.38 logs respectively. The seeds incubated at 40° F., alternatively, resulted in far lower average counts on all the pull days, and were below the detectable limit for the MPN and direct plate methods by Shelf Life Day 21.

The data indicated that the type of soaking treatments conducted in this Example did not have a significant impact

TABLE 8

| Treatment | Salmonella (MPN/g) or (CFU) | $Log_{10}$ (Salmonella MPN/g) or (CFU) | L. monocytogenes (MPN/g) or (CFU) | $Log_{10}$ (L. monocytogenes MPN/g) or (CFU) | E. coli O157:H7 (MPN/mL) or (CFU) | $Log_{10}$ (E. coli O157:H7 MPN/g) or (CFU) |
|---|---|---|---|---|---|---|
| Inoculation Culture | 3,800,000 | 6.58 | 4,000,000 | 6.60 | 9,900,000 | 7.00 |
| Day 0 Inoculated Controls | 80,804 | 4.91 | 758 | 2.88 | 199,633 | 5.30 |
| Inoculated Kerry 5011 (0.25% DWV) After 12 Days at 50° F., Shelf Life Day 0 at 40° F. | 1,100 | 3.04 | 430 | 2.63 | 1,100 | 3.04 |
| Shelf Life Day 7 at 40° F. | 1,100 | 3.04 | 240 | 2.38 | 24,000 | 4.38 |
| Shelf Life Day 14 at 40° F. | 1,500 | 3.18 | 930 | 2.97 | 46,000 | 4.66 |
| Shelf Life Day 21 at 40° F. | 93 | 1.97 | 11,000* | 4.04 | 43,000 | 4.63 |
| Shelf Life Day 28 at 40° F. | 120 | 2.08 | 15,000 | 4.18 | 43,000 | 4.63 |

*Actual Count is >1.1E+4

Figure 7:
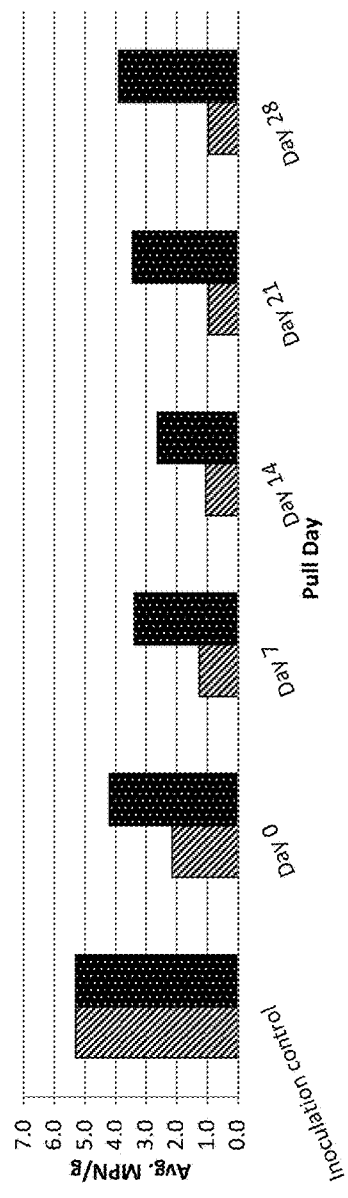
FIG. 7 is a bar graph of the effect of temperature on growth of sprouts for *E. coli* O157:H7.
Figure 8:
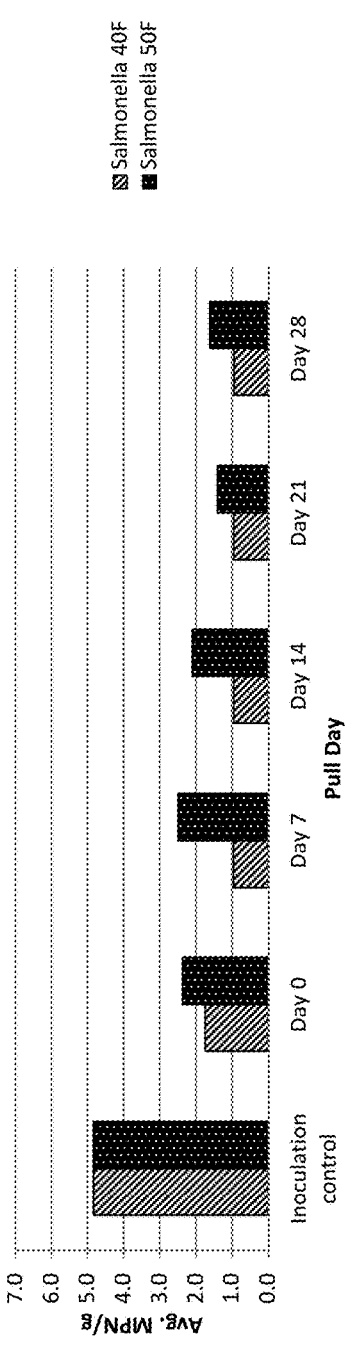
FIG. 8 is a bar graph of the effect of temperature on growth of sprouts for *Salmonella*.
Figure 9:
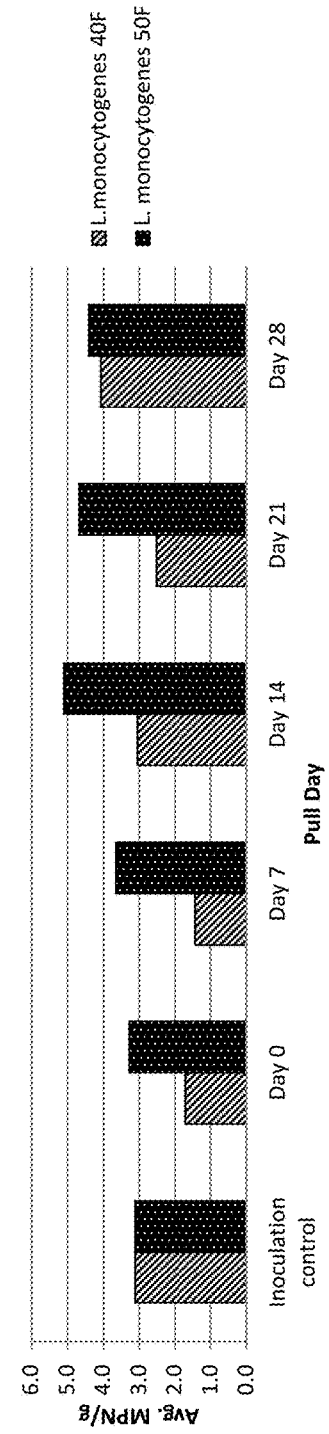
FIG. 9 is a bar graph of the effect of temperature on growth of sprouts for *Listeria*.
Figure 10:
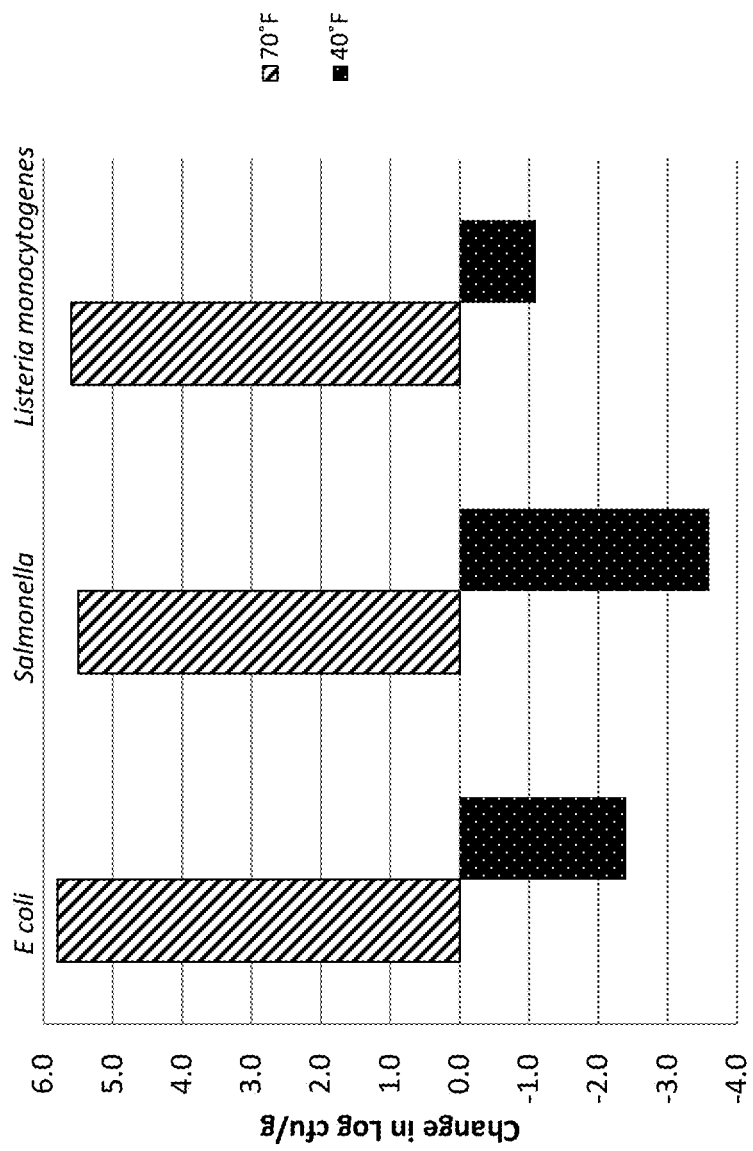
FIG. 10 is a bar graph of the change in the number of pathogens in the sprouts during the growth phase.

Table 8 details the results for the seed exposed to Kerry 5011 (0.25%), incubated at 50° F. for 12 days, then held at 40° F. through Shelf Life Day 28. The direct plate counts for all three organisms were obscured by the heavy growth of on the growth of the pathogens. The temperature that the sprouts were incubated impacted the growth of the pathogens. See FIGS. 7-9. The treatments were averaged together utilizing either the direct counts or the MPN values (whichever was appropriate e.g. if direct count was obscured by background flora the MPN value was used) for both temperatures. The results are illustrated in the bar graphs of FIGS. 7-9. FIG. 10 summarizes the results of the temperature treatment.

Conclusion

The main contributing factor in the growth of the pathogens based on this study is the temperature that the sprouts are grown and held. The two treatments (Acetic Acid (0.6% DWV, and Kerry 5011) did not appear to have a significant impact on the counts in comparison to the Control treatment.

When analyzing log differences it should be noted that slight changes in log reduction/growth (especially those <0.5 logs) are consistent with normal microbial variation and are generally not considered to be significant differences e.g. *L. monocytogenes* 50° F. Shelf Life Day 0 and Day 7, log difference 0.27 logs.

The levels of *Salmonella* spp. declined below the detectable limit for all three treatments incubated at 40° F. for 21 days and held at 40° F., a nearly 4 log reduction from the Day 0 inoculated controls, whereas the sprouts incubated at 50° F. had an average of 1.92 logs (approx. 83 MPN/g) present via the MPN method at Shelf Life Day 28.

The *E. coli* O157:H7 declined below the detectable limit in the cryo-sprouts incubated at 40° F. for 21 days via the MPN method for all three treatments (avg. log reduction of approx. 4 logs) at Shelf Life Day 21, however, very low levels were detected via direct plating in one of the Shelf life Day 28 samples (10 cfu/g, avg. log 0.97). Whereas the sprouts incubated at 50° F. had higher levels throughout the study with an average of 3.89 logs (7,760 MPN/g) present at Shelf Life Day 28 for the combined treatments via the MPN method.

The levels of *L. monocytogenes* increased by approx. 1 log from the control level in the sprouts incubated at 40° F. for 21 days when all three treatments are averaged together (avg. log value 4.07). The growth of *L. monocytogenes* at lower temperatures is not unexpected as it is known to be a psychrotroph, capable of growing at refrigeration temperatures. The sprouts incubated at 50° resulted in an average log value of 4.41 for the combined treatments, which was only slightly higher (0.34 logs) than that of the sprouts incubated at 40° F. at Shelf Life Day 28. It should be noted however that all of these results demonstrate significantly less growth than occurs when sprouts are grown at 70 F, at which temperature there was over a 5 log increase.

FIG. 10 demonstrates that the change in the targeted pathogenic bacteria is negative when the sprouts are grown at the pathogen antagonistic temperature and significantly positive when grown at ambient temperature. Sprouts inoculated with pathogenic bacteria and grown at 70° F. saw a greater than 5 log increase in pathogenic bacteria, whereas sprouts inoculated with pathogenic bacteria and grown at 40° F. exhibited a one to three log decrease during the growth period.

Figure 11:
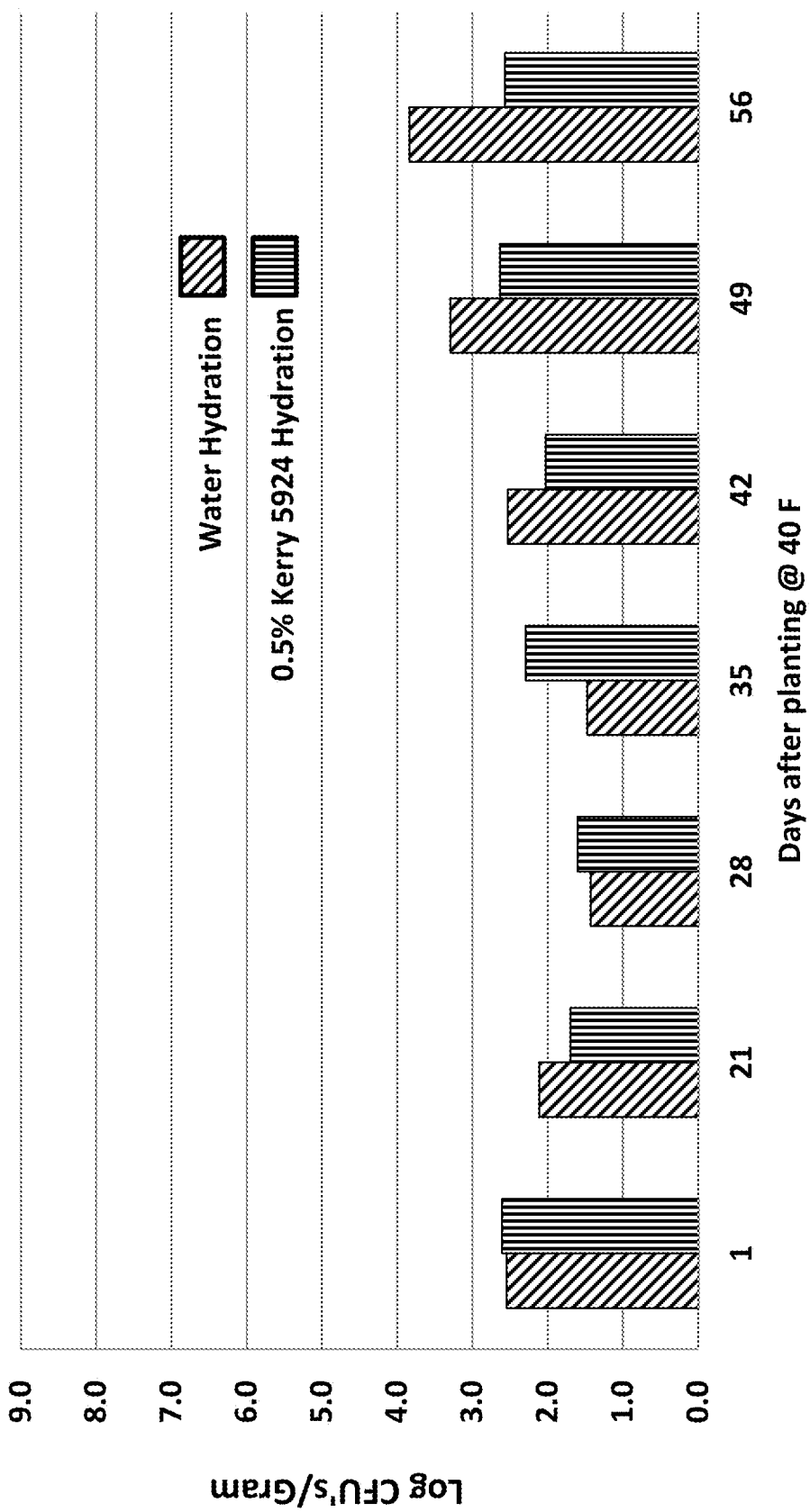
FIG. 11 is a bar graph of the effect of hydration compositions on the number of *Listeria monocytogenes* in the cryo-sprouts.

FIG. 11 demonstrated that hydration of the seeds in Kerry 5924 purchased from KERRY GROUP in Beloit, Wis. Kerry 5924 is a lactic acid bacterial fermentate wherein the fermentate includes nisin as a fermentation product. The addition of Kerry 5924 during hydration at a concentration of about 0.5% provided some additional inhibition of *Listeria monocytogenes* at 40° F. during extended shelf-life of the cryo-sprouts.

Example 2

The effect of static priming on the subsequent growth of cryo-sprouts was examined. The priming was done for 0, 1 or 2 weeks at 40° F. The seeds were disinfected and hydrated (1:1). The hydrated seeds were held in the standard growth trays with pads. (4 vent holes per tray). The seeds were added to a depth of about 1.5". All of the priming was done in the dark.

All of the seed varieties were purchased from CAUDILL SEED CO. INC. in Louisville, Ky., except where noted. The seeds were Alfalfa, Broccoli, Crimson Clover, Kale, Dwarf Siberian, Radish, Red Arrow.

Following planting (35 grams of seeds plus 60 grams water) the trays were held at 40° F., with light. There were 4 replicates at each condition. Observations and measurements of the average height of the nanogreens were taken weekly for 3 weeks. The results are in the shown in Table 9 below.

TABLE 9

| | Wks Primed | Centimeters Height (average) Grow @ 40 F. | | | Comments |
|---|---|---|---|---|---|
| | | 1 wk | 2 wk | 3 wk | |
| Alfalfa | 0 | 1.4 | 3.8 | 4.0 | |
| | 1 | 2.3 | 4.0 | 4.0 | |
| | 2 | 2.5 | 4.0 | 4.0 | |
| Broccoli | 0 | 0.6 | 0.6 | 0.6 | |
| | 1 | 0.8 | 2.5 | 4.0 | |
| | 2 | 2.0 | 4.0 | 4.0 | |
| Clover | 0 | 1.6 | 3.6 | 4.0 | |
| | 1 | 3.0 | 4.0 | 4.0 | |
| | 2 | 1.8 | 3.0 | 4.0 | (low % germination) |
| Kale (DS) | 0 | 0.6 | 2.2 | 4.0 | |
| | 1 | 1.6 | 3.6 | 4.0 | |
| | 2 | 2.4 | 4.0 | 4.0 | |
| Radish (RA) | 0 | 0.6 | 3.0 | 4.0 | |
| | 1 | 3.0 | 4.0 | 4.0 | |
| | 2 | 3.5 | 4.0 | 4.0 | |

Conclusions:

Priming appears necessary for Broccoli to germinate and grow at the pathogen antagonistic temperature. For varieties which do work without priming, priming can be used to decrease the "grow" time. The "grow" time can be reduced from about 3 weeks to about 2 weeks.

Priming of the seeds can be advantageous for several reasons. Priming can decouple the disinfection and hydration steps from planting thus increasing manufacturing flexibility. The area required for priming is ~$\frac{1}{10}^{th}$ that used once the trays are planted. Thus, priming can significantly increase plant capacity.

It is also possible that priming can be performed for too long for some seeds. For example, 2 weeks of priming on Crimson Clover was detrimental to % germination and growth rate as compared to 1 week.

Although the present invention has been described with reference to preferred embodiments, workers skilled in the art will recognize that changes may be made in form and detail without departing from the spirit and scope of the invention.

What is claimed is:

1. A covered container with cryo-sprouts comprising:
   a container comprising a membrane supported above a floor of the container on internal supports;
   seeds disposed on the membrane;
   water in the container, the amount of water sufficient for germination and growth of the seeds into cryosprouts; and a lid covering the container and forming an air permeable seal between the lid and the container, wherein the air permeable seal is configured for the permeation of air during germination of seeds and growth into cryo-sprouts, wherein the seeds germinate and grow into cryo-sprouts in the covered container at a pathogen antagonistic temperature below about 45° F., wherein the covered container comprises all of the water needed by the seeds for germination of the seeds and growth into the cryo-sprouts prior to covering with the lid, wherein the permeability to air in the covered container consists of permeability through the air permeable seal between the lid and the container.

2. The covered container of claim 1 wherein the cryo-sprouts are alfalfa, cress, radish, kale, clover, broccoli or combinations thereof.

3. The covered container of claim 1 wherein the membrane comprises woven material, non-woven material or combinations thereof.

4. The covered container of claim 1 wherein the pathogen antagonistic temperature is between about 35° F. and about 45° F.

5. The covered container of claim 1 wherein the cryo-sprouts are derived from about 15 grams to about 60 grams of air-dried seeds.

6. The covered container of claim 1 wherein the shelf-life of the cryo-sprouts is at least about 21 days.

7. The covered container of claim 1 wherein the shelf-life of the cryo-sprouts is at least about 15 days.

8. The covered container of claim 1 wherein the seeds are hydrated seeds.

9. The covered container of claim 1 wherein the covered container cannot form an air-tight sealed container.

10. The covered container of claim 1 wherein the covered container comprises all of the water needed for the seeds to grow into the cryo-sprouts.

11. The covered container of claim 1 wherein the covered container is permeable to light.

12. The covered container of claim 1 wherein the covered container comprises from about 2 grams water per gram of air-dried seeds to about 10 grams water per gram of air-dried seeds.

* * * * *